(12) United States Patent
Lloret Soler et al.

(10) Patent No.: US 9,976,844 B2
(45) Date of Patent: May 22, 2018

(54) MINIATURIZED OCT PACKAGE AND ASSEMBLY THEREOF

(71) Applicant: MEDLUMICS S.L., Tres Cantos-Madrid (ES)

(72) Inventors: Juan Lloret Soler, Madrid (ES); Juan Sancho Durá, Canals (ES); José Luis Rubio Guivernau, Madrid (ES); Eduardo Margallo Balbás, Madrid (ES); William Kennedy Landles, Toronto (CA); Andrés Cifuentes, Barcelona (ES); Blair Ungar, West Henrietta, NY (US); Kirill Zinoviev, Madrid (ES)

(73) Assignee: Medlumics S.L., Tres Cantos-Madrid (ES)

( * ) Notice: Subject to any disclaimer, the term of this patent is extended or adjusted under 35 U.S.C. 154(b) by 0 days. days.

(21) Appl. No.: 15/014,148

(22) Filed: Feb. 3, 2016

(65) Prior Publication Data

US 2016/0238371 A1    Aug. 18, 2016

Related U.S. Application Data

(60) Provisional application No. 62/113,170, filed on Feb. 6, 2015.

(51) Int. Cl.
*G01B 9/02* (2006.01)
*A61B 5/00* (2006.01)
(Continued)

(52) U.S. Cl.
CPC ........ *G01B 9/02051* (2013.01); *A61B 5/0066* (2013.01); *G01B 9/02091* (2013.01);
(Continued)

(58) Field of Classification Search
CPC .............. G01B 9/02049; G01B 9/0205; G01B 9/02051
See application file for complete search history.

(56) References Cited

U.S. PATENT DOCUMENTS

9,310,185 B2    4/2016  Soler et al.
9,310,563 B2    4/2016  Guivernau et al.
(Continued)

FOREIGN PATENT DOCUMENTS

JP    2002-221638 A    8/2002
JP    2003-228031 A    8/2003
(Continued)

OTHER PUBLICATIONS

International Search Report and Written Opinion directed to related International Patent Application No. PCT/EP2016/052549, dated Sep. 5, 2016; 11 pages.
(Continued)

*Primary Examiner* — Jonathan Hansen
(74) *Attorney, Agent, or Firm* — Sterne, Kessler, Goldstein & Fox P.L.L.C.

(57) ABSTRACT

A chip package includes a housing, one or more electrical connections coupled to an exterior of the housing, a photonic integrated circuit, and a scanning unit. Both the photonic integrated circuit and the scanning unit are disposed within the housing. The photonic integrated circuit has at least one waveguide designed to guide a beam of light. The scanning unit is designed to laterally scan the beam of light across a focal plane outside of the housing. The scanning unit is aligned with the photonic integrated circuit such that the beam of light is coupled between the photonic integrated circuit and the scanning unit.

23 Claims, 32 Drawing Sheets

(51) Int. Cl.

| | |
|---|---|
| *G02B 6/30* | (2006.01) |
| *G02B 6/27* | (2006.01) |
| *G02B 6/32* | (2006.01) |
| *G02B 6/42* | (2006.01) |
| *G02B 26/08* | (2006.01) |
| *G02B 6/293* | (2006.01) |

(52) U.S. Cl.
CPC ............ G02B 6/2766 (2013.01); G02B 6/30 (2013.01); G02B 6/32 (2013.01); G02B 6/4251 (2013.01); G02B 6/4284 (2013.01); G02B 26/0833 (2013.01); *A61B 2562/0233* (2013.01); *A61B 2562/228* (2013.01); *G02B 6/29346* (2013.01); *G02B 6/4221* (2013.01); *G02B 6/4226* (2013.01); *G02B 6/4269* (2013.01); *G02B 6/4271* (2013.01)

(56) References Cited

U.S. PATENT DOCUMENTS

| | | |
|---|---|---|
| 9,354,040 B2 | 5/2016 | Guivernau et al. |
| 9,366,885 B2 | 6/2016 | Guivernau et al. |
| 2004/0033016 A1 | 2/2004 | Kropp |
| 2005/0011199 A1* | 1/2005 | Grisham ................. F25B 21/02 62/3.7 |
| 2009/0122383 A1* | 5/2009 | Reyes ................... G01J 3/4535 359/238 |
| 2011/0292399 A1 | 12/2011 | Alphonse |
| 2012/0170046 A1 | 7/2012 | Flanders |
| 2014/0092388 A1 | 4/2014 | Lee et al. |
| 2014/0264400 A1* | 9/2014 | Lipson .................. H01L 27/144 257/88 |
| 2014/0293290 A1* | 10/2014 | Kulkarni ............ G01B 9/02091 356/479 |
| 2014/0376001 A1 | 12/2014 | Swanson |
| 2015/0185415 A1 | 7/2015 | Zinoviev et al. |

FOREIGN PATENT DOCUMENTS

| | | |
|---|---|---|
| JP | 2004-117706 A | 4/2004 |
| JP | 2011-523460 A | 8/2011 |
| WO | WO 2014-129613 A1 | 2/2017 |

OTHER PUBLICATIONS

Yurtsever et al., "Photonic Integrated Mach-Zehnder Interferometer With an On-Chip Reference Arm for Optical Coherence Tomography," Biomedical Optics Express, vol. 5, No. 4, Apr. 1, 2014, XP055266229; 12 pages.

Schneider et al., "Silicon Photonic Optical Coherence Tomography System," 2014 Conference on Lasers and Electro-Optics (CLEO)—Laser Science to Photonic Applications, The Optical Society, Jun. 8, 2014, XP032707079; pp. 1-2.

Japanese Office Action dated Dec. 26, 2017 directed to App. No. 2017-541639, with attached English language translation, 10 pages.

* cited by examiner

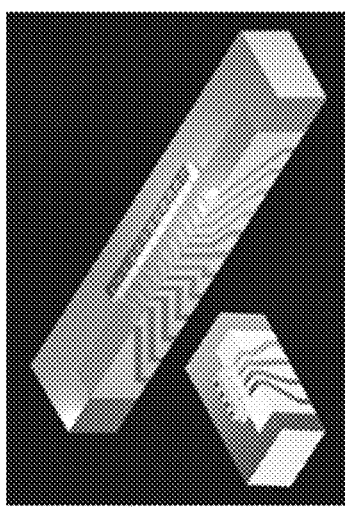
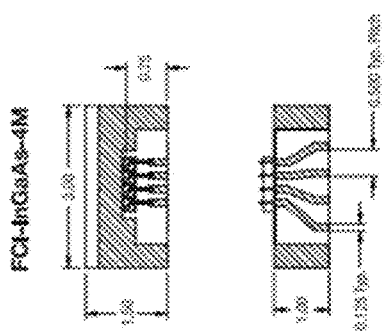
FIG. 3

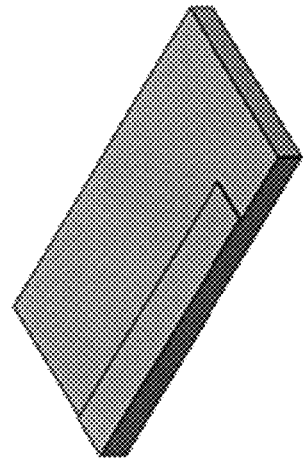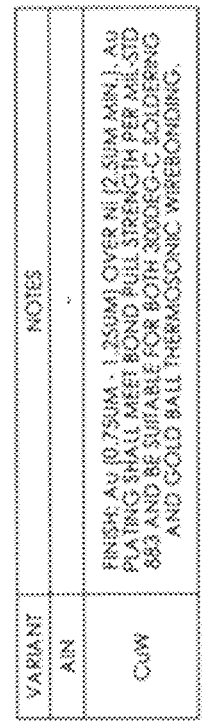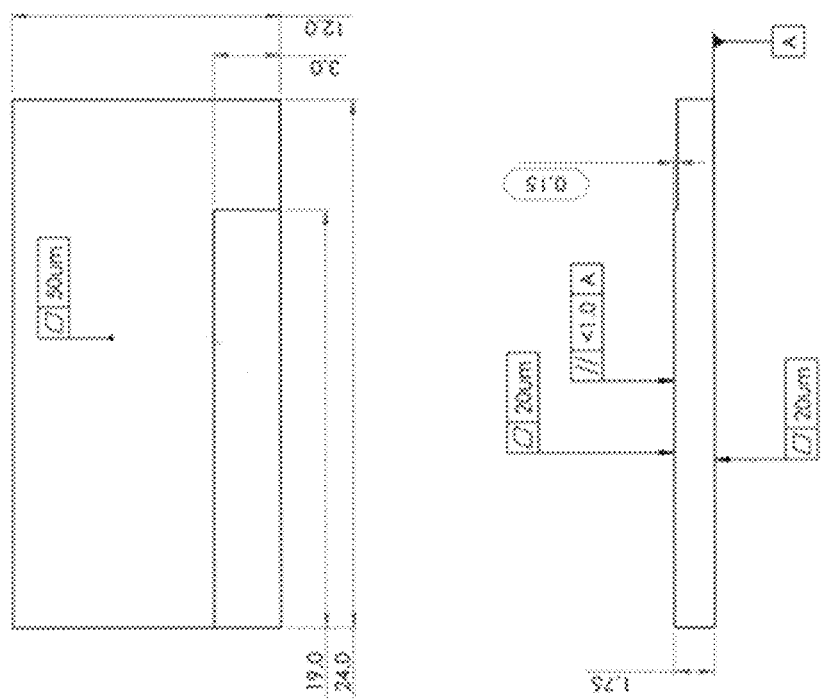
FIG. 4

MINIATURIZED OCT PACKAGE AND ASSEMBLY THEREOF

CROSS-REFERENCE TO RELATED APPLICATIONS

This application claims the benefit of U.S. Provisional Application No. 62/113,170 filed Feb. 6, 2015, the disclosure of which is incorporated by reference herein in its entirety.

BACKGROUND

Field

Embodiments of the invention relate to designs of a miniaturized OCT system.

Background

Optical coherence tomography (OCT) is an imaging technique that is widely used in many fields to provide depth-revolved imaging of various samples. The technique has found widespread use in the medical field where OCT data is used on skin and tissue to help diagnose various ailments as well as provide enhanced visual feedback to medical practitioners. Miniaturization of an OCT system is difficult due to the number of components required and the high coupling sensitivities between optical elements.

BRIEF SUMMARY

In the embodiments presented herein, designs of an integrated, miniaturized OCT system, and methods for fabricating such a system, are presented.

In an embodiment, a chip package includes a housing, one or more electrical connections coupled to an exterior of the housing, a photonic integrated circuit, and a scanning unit. Both the photonic integrated circuit and the scanning unit are disposed within the housing. The photonic integrated circuit has at least one waveguide designed to guide a beam of light. The scanning unit is designed to laterally scan the beam of light across a focal plane outside of the housing. The scanning unit is aligned with the photonic integrated circuit such that the beam of light is coupled between the photonic integrated circuit and the scanning unit.

In another embodiment, a method includes attaching a heat sink to one side of a photonic integrated circuit, and attaching an opposite side of the heat sink to a base of a package. The method further includes attaching a photo detector to the heat sink. The method also includes attaching a fiber mount to the heat sink. The fiber mount holds, and aids in the alignment of, optical fibers within the package. The method also includes attaching a scanning unit to the base of the package, where the attaching of the scanning unit, the attaching of the fiber mount, and the attaching of the photo detector align the photonic integrated circuit, photo detector, fiber mount, and scanning unit so as to maximize a coupling efficiency of a beam of light traveling between the photonic integrated circuit, photo detector, fiber mount, and scanning unit.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 3 illustrates example electro-optical characteristics of a photo diode array.

FIG. 4 illustrates a heat spreader element, according to an embodiment.

Embodiments of the present invention will be described with reference to the accompanying drawings. Although some of the drawings may include specific measurements, dimensions, and/or photographs of prototype parts, such specifics are not to be considered limiting to the scope of the invention. Rather, the drawings provide example embodiments of the invention.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments herein relate to a design and method of making an integrated chip package. The package may include various optical, opto-electrical, and electrical elements designed to perform image acquisition using techniques such as optical coherence tomography (OCT). Herein, the terms "electromagnetic radiation," "light," "beam of radiation," and "optical beam" are all used to describe the same electromagnetic signals propagating through the various described elements and systems.

Figure 1:
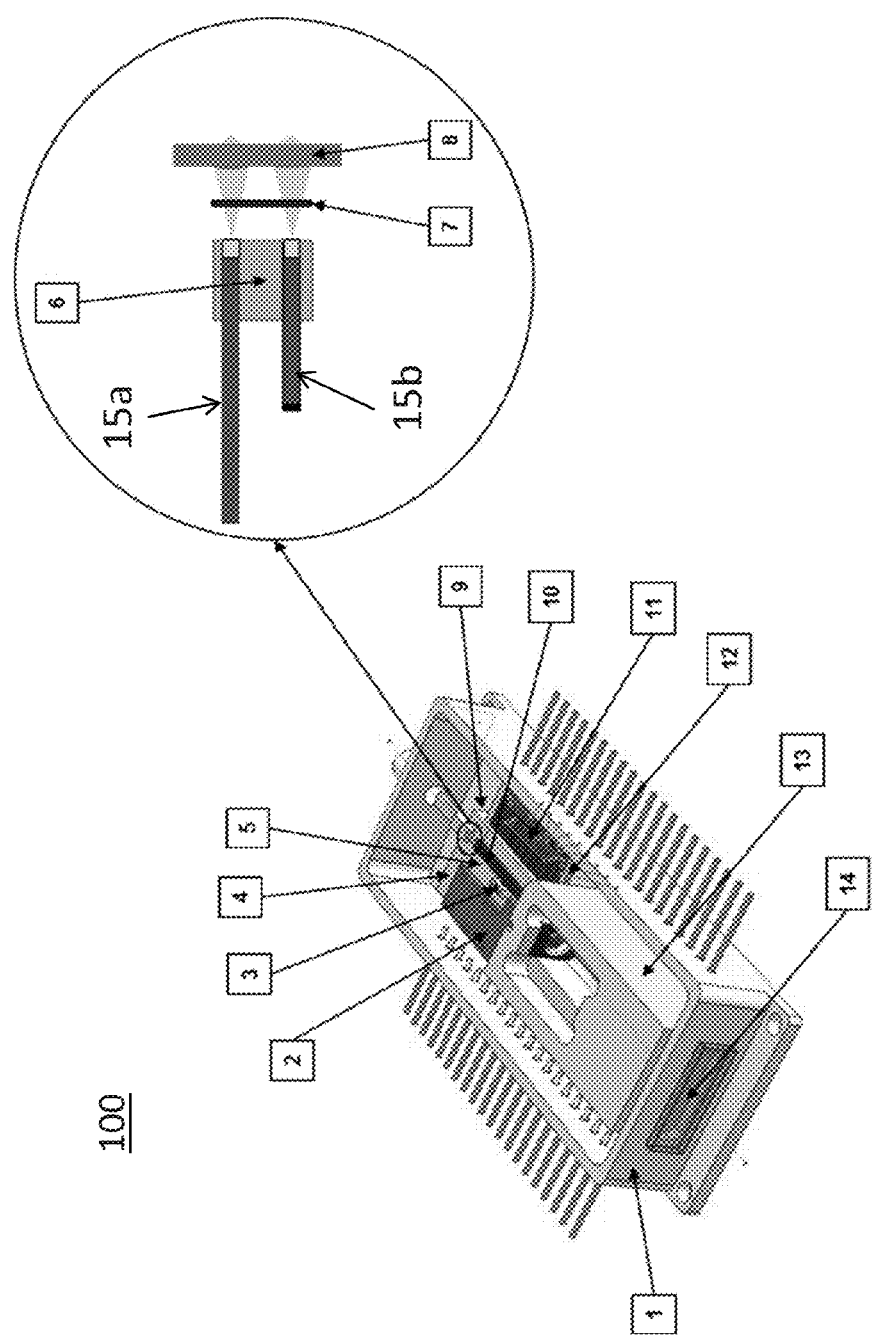
FIG. 1 illustrates a chip package, according to an embodiment.
Figure 2:
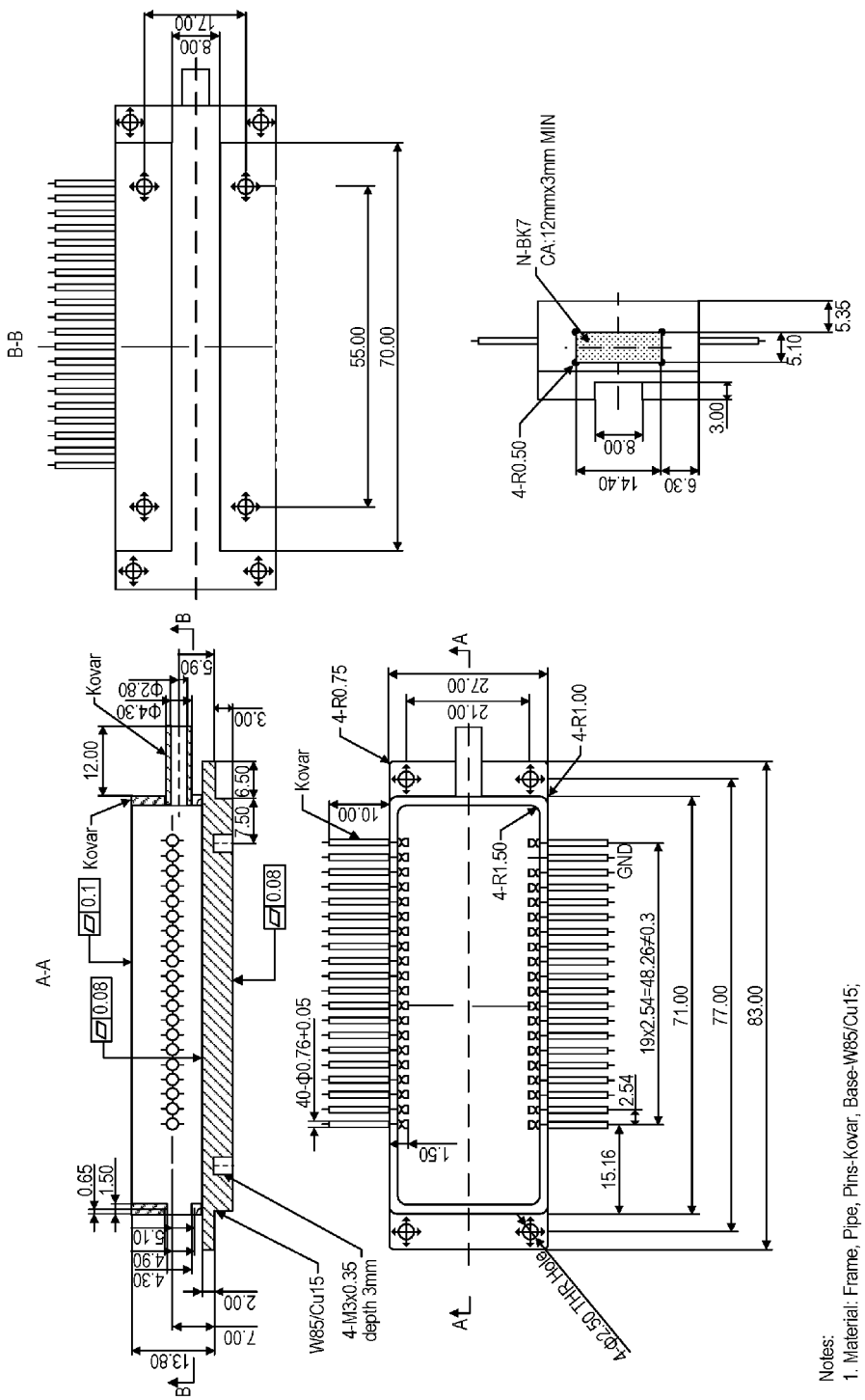
FIG. 2 illustrates example dimensions of a chip package.

FIG. 1 illustrates a layout of a chip package 100, according to an embodiment. In one example, chip package 100 is a 40-pin butterfly-type package. Chip package 100 includes a housing 1 that surrounds the various elements disposed inside. An example design drawing of chip package 100 is illustrated in FIG. 2. Chip package 100 includes a circuit board 2. Circuit board 2 may be used to amplify detected OCT signals before being connected to the package pins. In addition, circuit board 2 may provide polarization voltage driving a photodiode array 3. In one example, photodiode array 3 includes an indium gallium arsenide (InGaAs) active layer. FIG. 3 provides example electro-optical characteristics of photodiode array 3.

Figure 8:
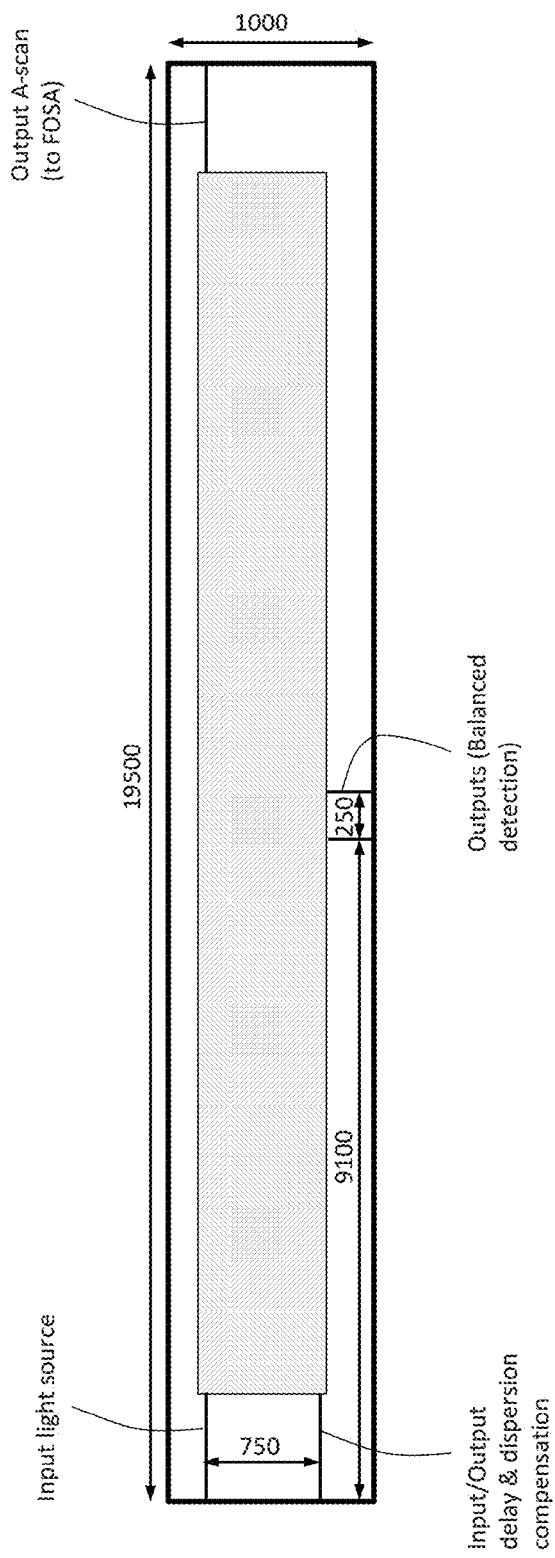
FIG. 8 illustrates inputs and outputs of a photonic integrated circuit, according to an embodiment.

Chip package 100 includes a photonic integrated circuit (PIC) 10, according to an embodiment. PIC 10 is manufactured by using a Silicon-On-Insulator (SOI) technology platform, in one example. PIC 10 may implement a full A-scan OCT system with a depth range of about 3 mm in air mediated by on-chip akinetic means. PIC 10 may include an interferometer arrangement to perform the OCT A-scan. The design wavelength may be around 1300 nm, although other IR wavelengths could be used as well. PIC 10 may implement 3 optical ports: one aimed to receive light from a light source, a second devoted to align an element intended to compensate both the delay and dispersion induced by a scanning unit 13 and a third one is used for injecting light into scanning unit 13, which performs the B-scan of the OCT system. Additionally, 2 optical ports may be implemented to provide balanced detection. An example sketch of PIC 10 is shown in FIG. 8. PIC 10 may include optical arrangements to provide an integrated delay line (for changing the scan depth) as well as to provide birefringence compensation of the light as it passes through the various waveguides. Furthermore, PIC 10 may include an optical arrangement to compensate for the effects of chromatic dispersion. More detailed examples of such optical arrangements to be implemented within PIC 10 can be found in co-pending U.S. application Ser. Nos. 14/129,367, 14/005,172, 14/299,725, and 14/584,592 the disclosures of which are incorporated by reference herein in their entireties.

Chip package 100 may also include a heat spreader 4. Heat spreader 4 may be a high-precision machined optical bench manufactured by a high thermal conductive material. In one design, AlN (aluminum nitride) is used. The decision on the material to be used is based on both the thermal conductivity and the coefficient of thermal expansion (CTE). The purpose is to spread the heat locally generated by PIC 10 into a larger footprint. This allows for higher cooling efficiency. Moreover, mechanical features may also be implemented to match the height between different parts to be aligned on top of the spreader. FIG. 4 shows an example mechanical drawing of the heat spreader 4, outlining two material variants.

Figure 5:
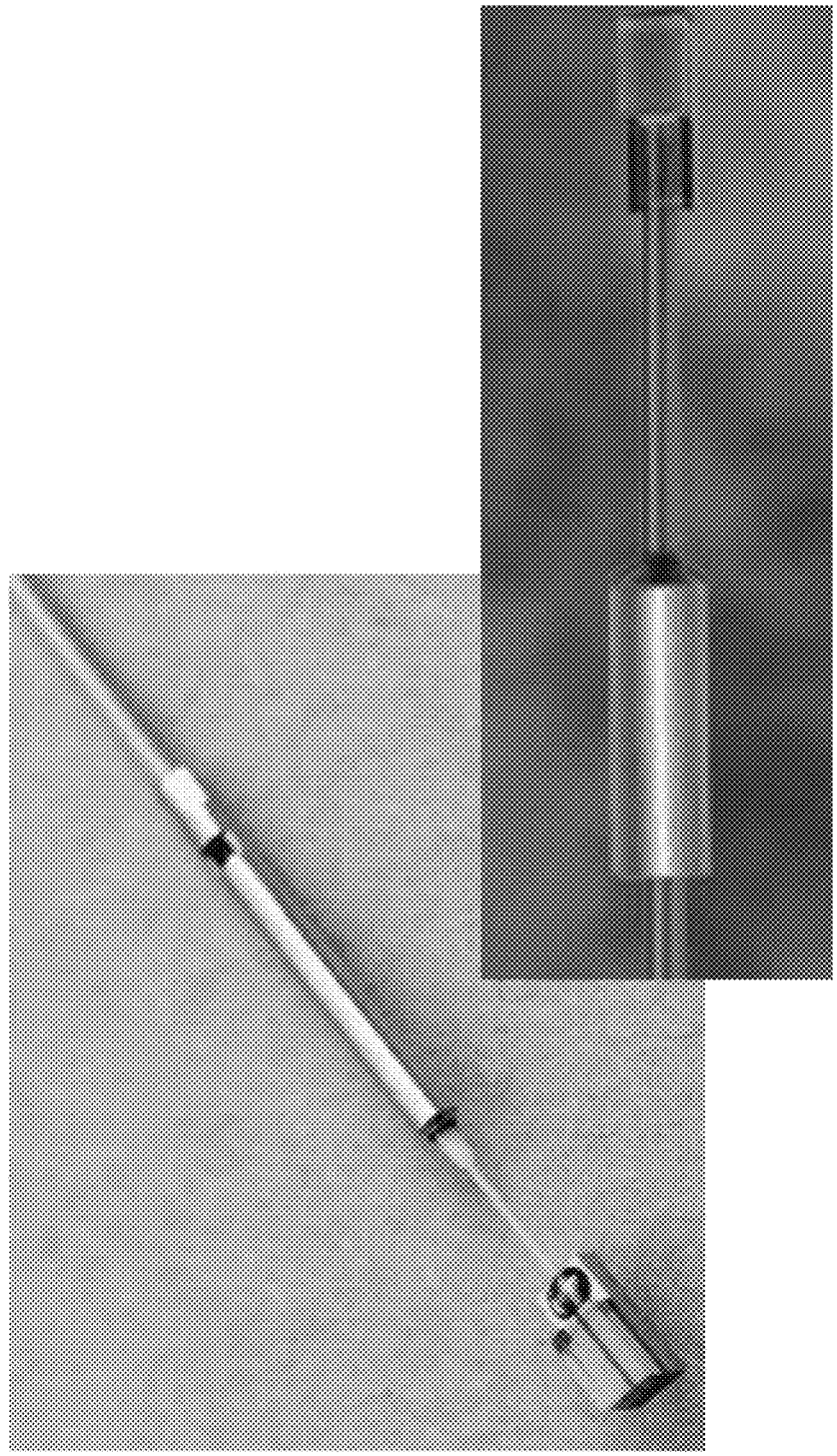
FIG. 5 illustrates a fiber mount structure, according to an embodiment.

Chip package 100 includes a thermistor 5, according to an embodiment. Chip package 100 also includes a fiber mount 6, according to an embodiment. Fiber mount 6 may be a v-groove chip for aligning one or more optical fibers 15a and 15b. A total pitch between two fibers on mount element 6 is around 750 urn, according to an embodiment. An antireflective coating with R<0.5%@1.32 μm±50 nm may be used on the fibers. The shorter fiber 15b may implement an end-mirrored facet based on Au or Ag. This fiber is intended to compensate both the delay and dispersion induced by scanning unit 13 within chip package 100. An exemplary drawing of a typical fiber v-groove array (FVA) with a hermetic ferrule is illustrated in FIG. 5. Fiber mount 6 may be designed to help align fiber 15a, delivering the source light, with a waveguide on PIC 10.

Figure 6:
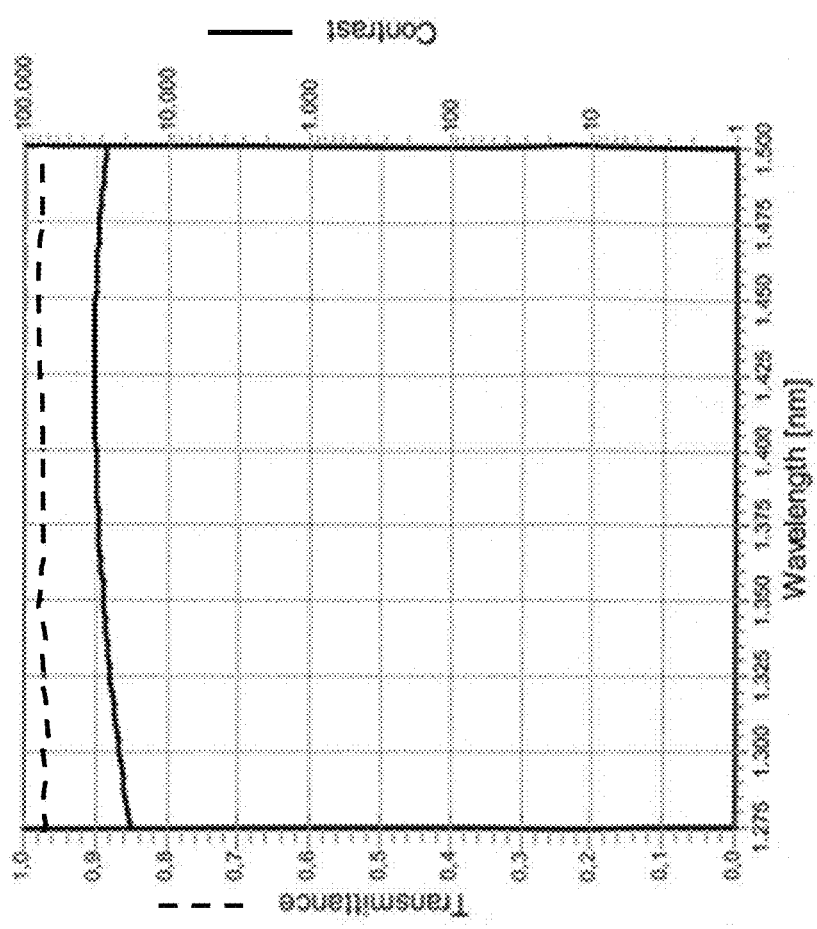
FIG. 6 illustrates an example spectral response of a polarizer.

Chip package 100 includes a polarizing element 7, according to an embodiment. Polarizing element 7 may be used for filtering the light which is not polarized with the main polarization axis. At detection, light featuring a polarization different from that defined by the main polarization axis will interfere and degrade the total SNR. FIG. 6 shows the spectral response in terms of transmittance and contrast of an example polarizing element 7.

Figure 7:
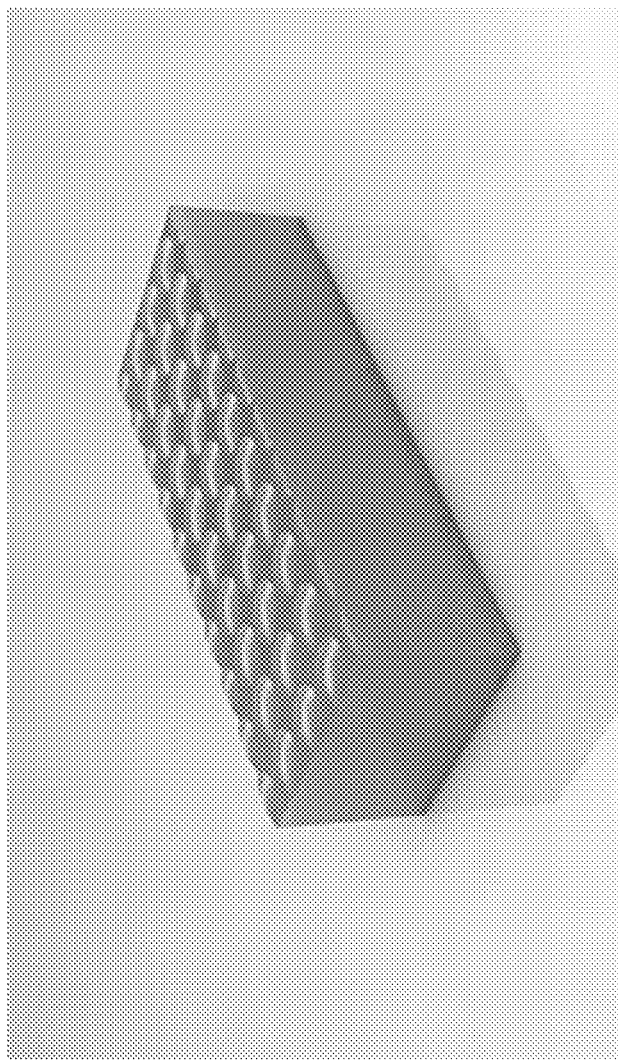
FIG. 7 illustrates a micro-lens array, according to an embodiment.

Chip package 100 includes a lens array 8, according to an embodiment. Lens array 8 may be a mirco-lens array having a 250 micron pitch between lens elements. The micro-optics may be used for matching the mode exiting the fiber with the propagation mode of the input waveguide on PIC 10, thus reducing coupling loss. The assembly of optics in-between the fiber and PIC 10 helps to relax the alignment tolerances as it will be described hereafter. FIG. 7 shows a 3D drawing of an arbitrary sized micro-lens array, according to an embodiment.

Chip package 100 includes a cooling element 9, according to an embodiment. Cooling element 9 may be a thermoelectric cooler. Cooling element 9 aims to keep stable the base temperature of PIC 10. Therefore, the optical performance dependence of the elements in the PIC 10 is controlled. Moreover, by keeping a fixed temperature on top of heat spreader 4, misalignments between parts on it due to thermal expansion properties attached may be avoided.

Chip package 100 may include a circuit board interposer 11. Interposer 11 aims to provide an electrical contact area enabling auxiliary connections. Interposer 11 may optimize the number of connections of the bonding map between PIC 10 and the pins of chip package 1. Moreover, the usage of interposer 11 results in shorter wires, thus reducing the probability of undesired contact between wires and lack of adhesion. An example of interposer 11 is a single-sided board, with ½ oz copper and standard FR4 construction.

Chip package 100 may include a block 12 used to adjust the height of interposer 11 to the same height as PIC 10. In one example, interposer 11 is attached on top of block 12. Block 12 may be machined from a metal, plastic, or polymer.

Figure 9:
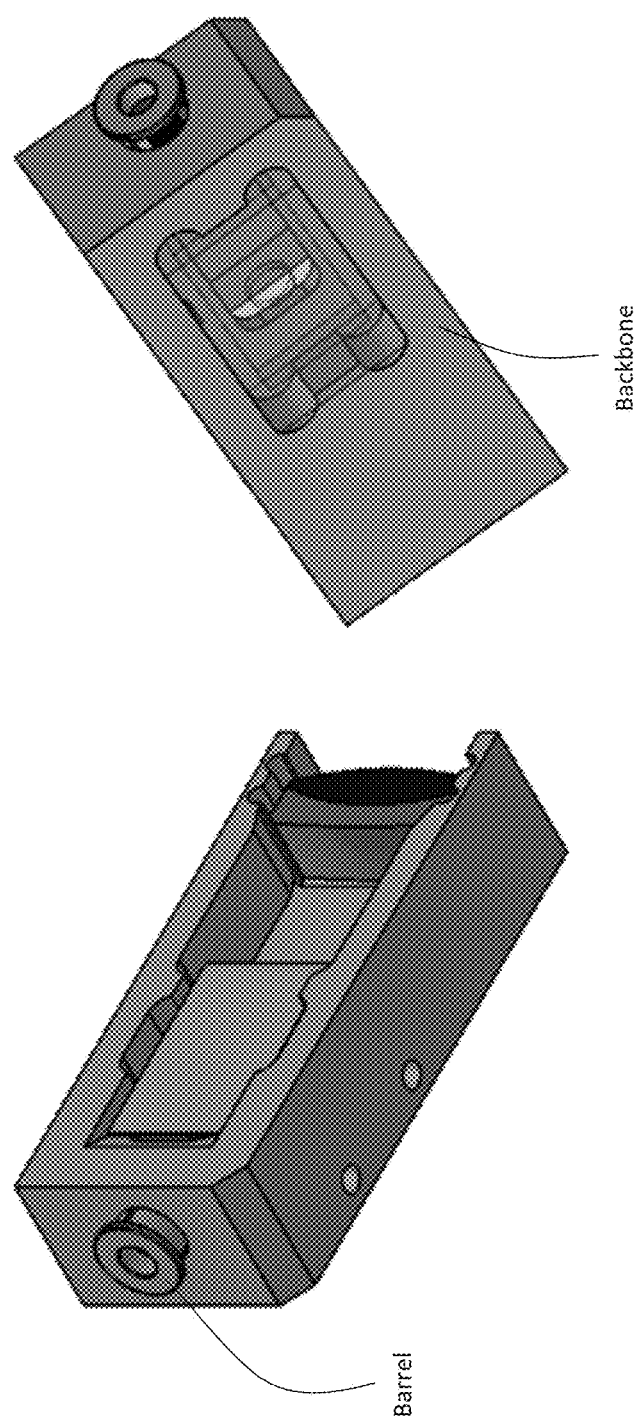
FIG. 9 illustrates a scanner device, according to an embodiment.

Chip package 100 includes a scanning unit 13, according to an embodiment. Scanning unit 13 implements the B-scan allowing for 2D OCT scanning together with the A-scan generated by PIC 10, according to an embodiment. Scanning unit 13 provides the desired scanning range (e.g., 12 mm) at the focal plane. Additionally, the lateral resolution is adjusted by scanning unit 13 along the scanning range, thus guaranteeing the desired depth of field. Scanning unit 13 may include a barrel (beam collimation) and a backbone (lateral scanning and beam focusing). Moreover, the total optical path of scanning unit 13 can be adjusted since the barrel can be moved back and forth along the backbone. This may be done to compensate the fabrication tolerances in the delay and dispersion compensating systems. FIG. 9 shows a 3D mechanical model of scanning unit 13, according to an embodiment. A detailed explanation of an example scanning unit may be found in co-pending U.S. application Ser. No. 14/118,629, the disclosure of which is incorporated by reference herein in its entirety.

Chip package 100 includes an optical window 14 within a side of housing 1, according to an embodiment. Optical window 14 includes a material chosen to be substantially transparent to IR wavelengths (e.g., borosilicate glass). Optical window 14 is also assembled with housing 1 to ensure a desired package hermeticity. FIG. 2 shows an example package design that includes a 14.4 mm×5.1 mm N-BK7 glass window. The dimensions are chosen to be compatible with the scanning field of view from scanning unit 13, according to an embodiment.

PIC 10 and scanning unit 13 are aligned within housing 1 of chip package 100, such that a beam of light is coupled between the photonic integrated circuit and the scanning unit. This coupling efficiency is maximized based on the alignment, according to an embodiment. Scanning unit 13 is also positioned such that it scans the beam of light across a focal plane outside of chip package 100. The scanned beam of light crosses through optical window 14.

Although not shown in FIG. 1, an optical source generates a beam of light that is delivered to chip package 100 via optical fiber 15*a*, according to an embodiment. The beam of light is output from fiber 15*a* and traverses both polarizer 7 and lens array 8 before being coupled into a waveguide on PIC 10, according to an embodiment. Fiber mount 6 is used to help align both fibers 15*a* and 15*b* with respective waveguides on PIC 10. As such, the arrangement including fiber mount 6, polarizer 7, and lens array 8 is provided to maximize coupling efficiency of the light between the waveguides on PIC 10, and the optical fibers. In another example, the optical source is integrated within chip package 100.

This invention helps solve many miniaturized packaging problems in order to make the PIC 10 resistant against moisture, shocks and thermally and mechanically harsh environments. Scanning unit 13 enabling B-scanning, and read-out electronics are also assembled within the same package, thus resulting in a fully-packaged 2D OCT system. Below, various design aspects of chip package 100 are described in further detail.

Light Coupling

Figure 10:
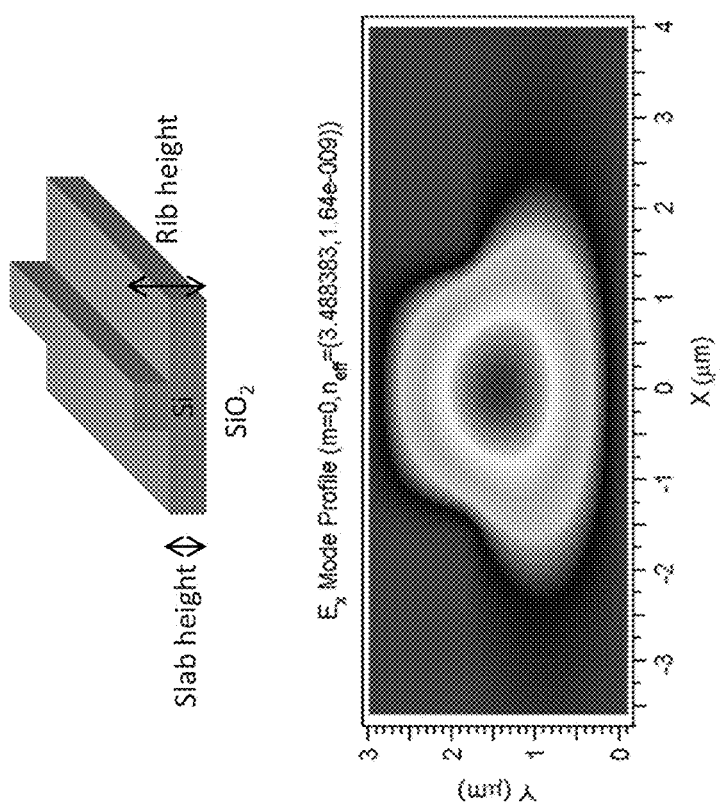
FIG. 10 illustrates an example rib waveguide and corresponding beam profile within the waveguide.
Figure 11:
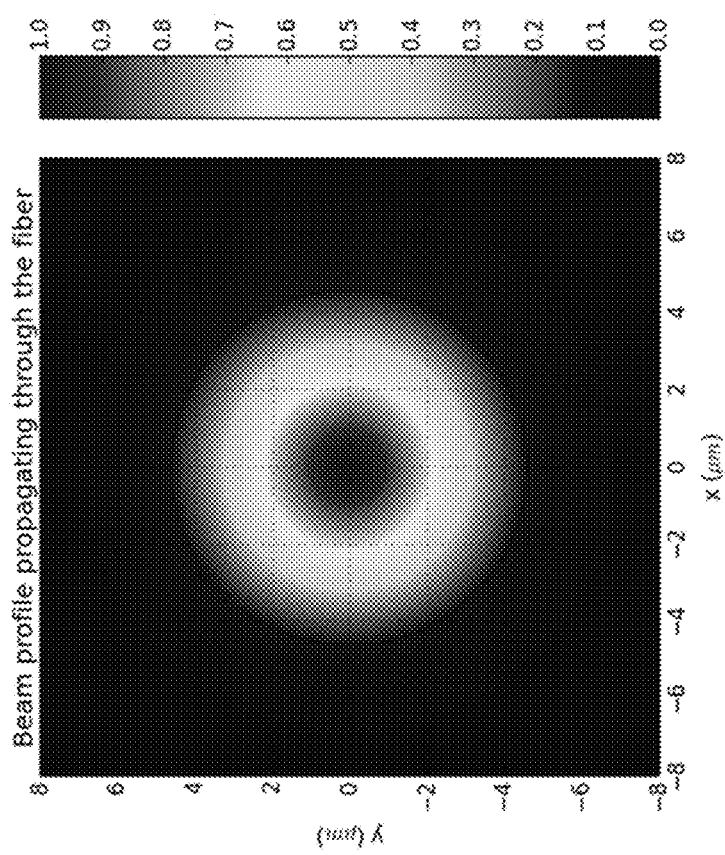
FIG. 11 illustrates an example beam profile through an optical fiber.

A large coupling efficiency is desired between the light source and the PIC 10. The facets in the ports of the PIC 10 are implemented by rib-type waveguides, according to an embodiment. The total height of the waveguide is around 3 with a slab height of around 1.8 µm, according to an embodiment. This fact translates into astigmatic propagation modes, thus resulting in different numerical apertures for the X and Y directions at the PIC 10 end-face (see FIG. 10). The beam profile of light propagating through an optical fiber is shown in FIG. 11. The coupling efficiency may be greatly increased by using substantially rounded modes with about the same numerical aperture for both axes in the waveguides on PIC 10.

The coupling efficiency is estimated by the overlap integral, which is defined as:

$$\Gamma = \frac{\left|\int_{-\infty}^{\infty}\int_{-\infty}^{\infty} E_{fiber}(x, y)E_{chip}(x, y)\,dx\,dy\right|^2}{\int_{-\infty}^{\infty}\int_{-\infty}^{\infty} |E_{fiber}|^2 dx\,dy \cdot \int_{-\infty}^{\infty}\int_{-\infty}^{\infty} |E_{chip}|^2 dx\,dy} \quad (1)$$

Where $E_{fiber}$ and $E_{chip}$ are the electrical field propagating through the optical fiber and the PIC input waveguide respectively. In this particular example, the coupling efficiency $\Gamma=27.25\%$ which translates into a coupling loss of 5.65 dB. This coupling loss is not acceptable to reach a large dynamic range in the OCT system. Thus, a mode matching between the beam exiting the optical fiber and the input waveguide is used to reduce the coupling loss, according to an embodiment.

Figure 12:
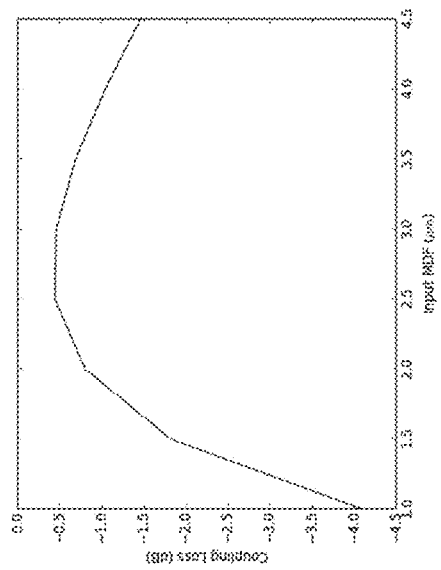
FIG. 12 illustrates an example coupling loss to a waveguide.
Figure 13:
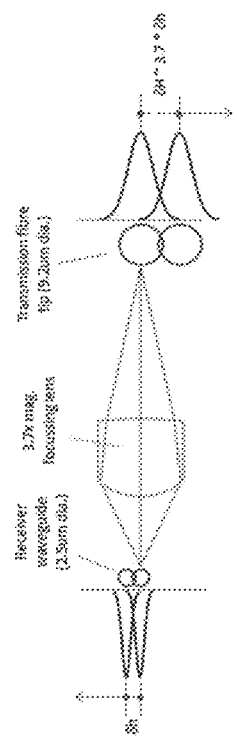
FIG. 13 illustrates example alignment tolerances between light guiding mediums.

FIG. 12 shows the coupling loss as a function of the mode field diameter (MFD) of the light beam launched into the PIC waveguide. Maximum coupling efficiency is reached when the input MFD is about 2.5 µm as derived from FIG. 12. The fact of using optics in-between the optical fibers and PIC waveguides implemented on a different substrate provides an extra degree of freedom for the alignment process. This extra degree of freedom can be used to optimize the coupling efficiency, since the relative position between the optical fibers and lens array 8 can be controlled. FIG. 13 shows how to benefit from the magnification given by the lens in order to relax the alignment tolerances. For simplicity, FIG. 13 only illustrates one of the four channels. In particular, a tolerance accuracy of δh at the waveguide input (MFD=SD=2.5 µm) is translated into a tolerance accuracy of m times δh at the fiber input (MFD=9.2 µm), where m is the lens magnification. In this case, the magnification may be set to 9.2/2.5=3.68.

Figure 14:
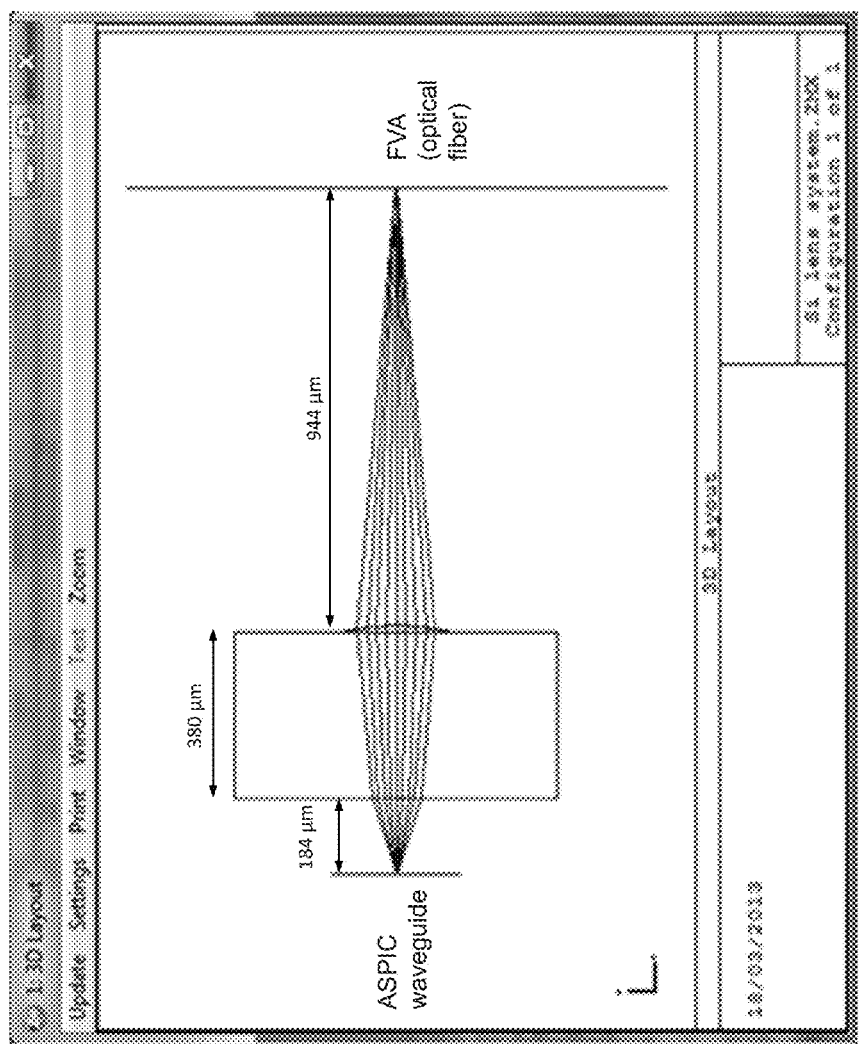
FIG. 14 illustrates an example simulation of light focusing.

FIG. 14 shows example ray-trace simulations and the design lengths of the fiber-to-chip focusing system. A coupling efficiency of up to 86% has been theoretically and experimentally demonstrated by using this solution. Consequently, this solution can meet a coupling requirement of <1 dB.

Other solutions such as butt coupling or lensed/tapered fiber v-groove array do not benefit from the above-mentioned advantage. On one hand, the alignment tolerances will be imposed by the accuracy of the align & attach process for butt coupling. Moreover, prohibited coupling loss larger than 5 dB is reached by this technique. On the other hand, apart from the accuracy of the align & attach process, the mechanical tolerances of the v-groove chip and fibers positioning could have a strong impact.

Figure 15:
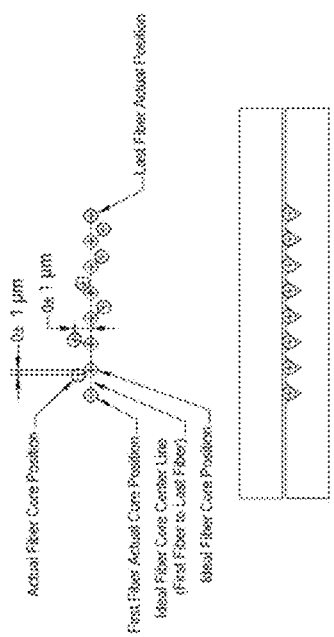
FIG. 15 illustrates example fiber alignment tolerances.
Figure 16:
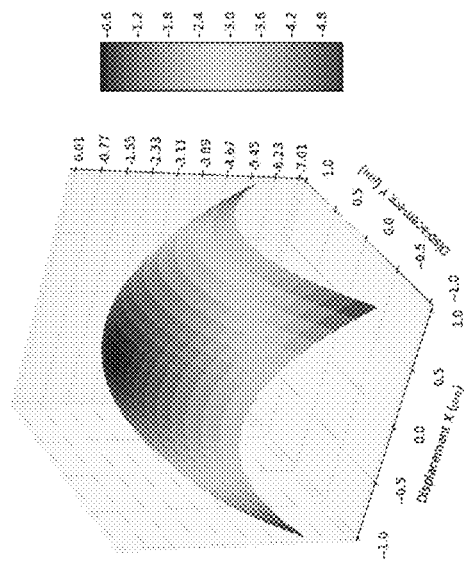
FIG. 16 illustrates simulated coupling losses into a waveguide, according to an embodiment.

FIG. 15 shows this effect. The typical tolerance of the fibers being assembled on an example v-groove chip is ±1 µm. FIG. 16 shows the coupling loss for a MFD of 2.5 µm when it is misaligned with respect to the waveguide. As depicted in FIG. 16, this tolerance is not acceptable to fulfill a coupling loss target of <1 dB.

The alignment between the PIC output waveguides (balanced detection) and the PIC is a key factor limiting the SNR performance of the OCT system. The separation distance between the waveguide end facets and photo-diode array 3 (hereafter referred as 's') depends on the numerical aperture of the waveguides, which is 0.39 for both the x and y coordinates, according to one example, and the accuracy of the alignment process. The spot diameter in the waveguide is calculated to be 2.3 µm for both the x and y coordinates respectively, in this example. On the other hand, the active area diameter of the photodiodes is 70 µm, according to one example.

Figure 17B:
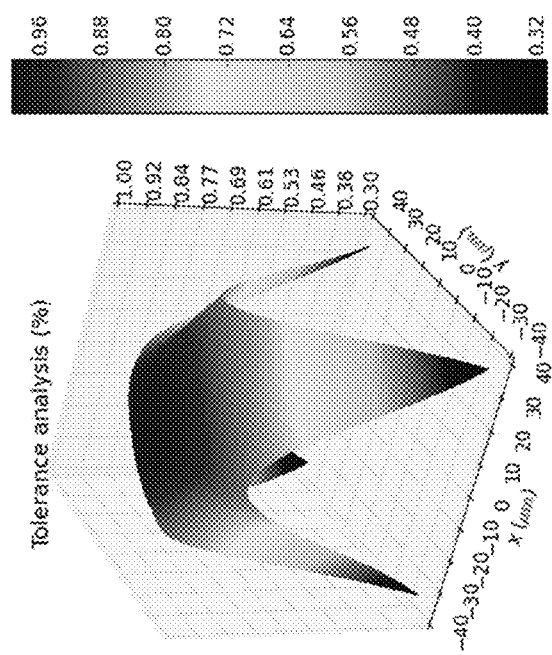
FIGS. 17A and 17B illustrate simulated coupling efficiencies, according to some embodiments.
Figure 17A:
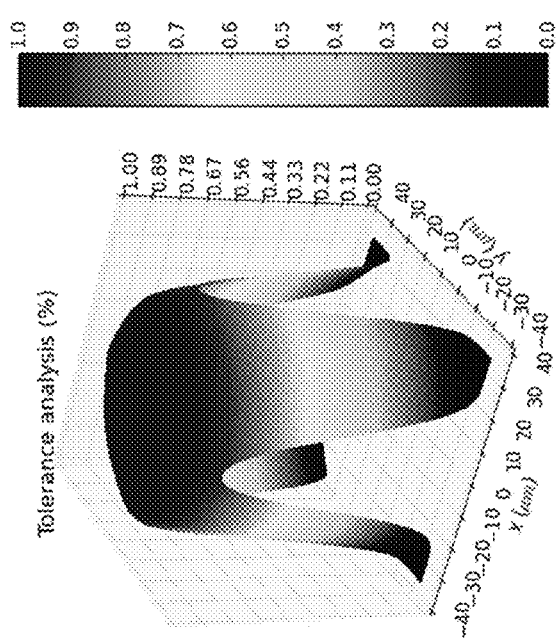

FIGS. 17A and 17B show 3D plots of the coupling efficiency for two different cases in which s=10 µm and s=50 respectively. As expected, the maximum tolerances become lower as the distance s increases.

Figure 18:
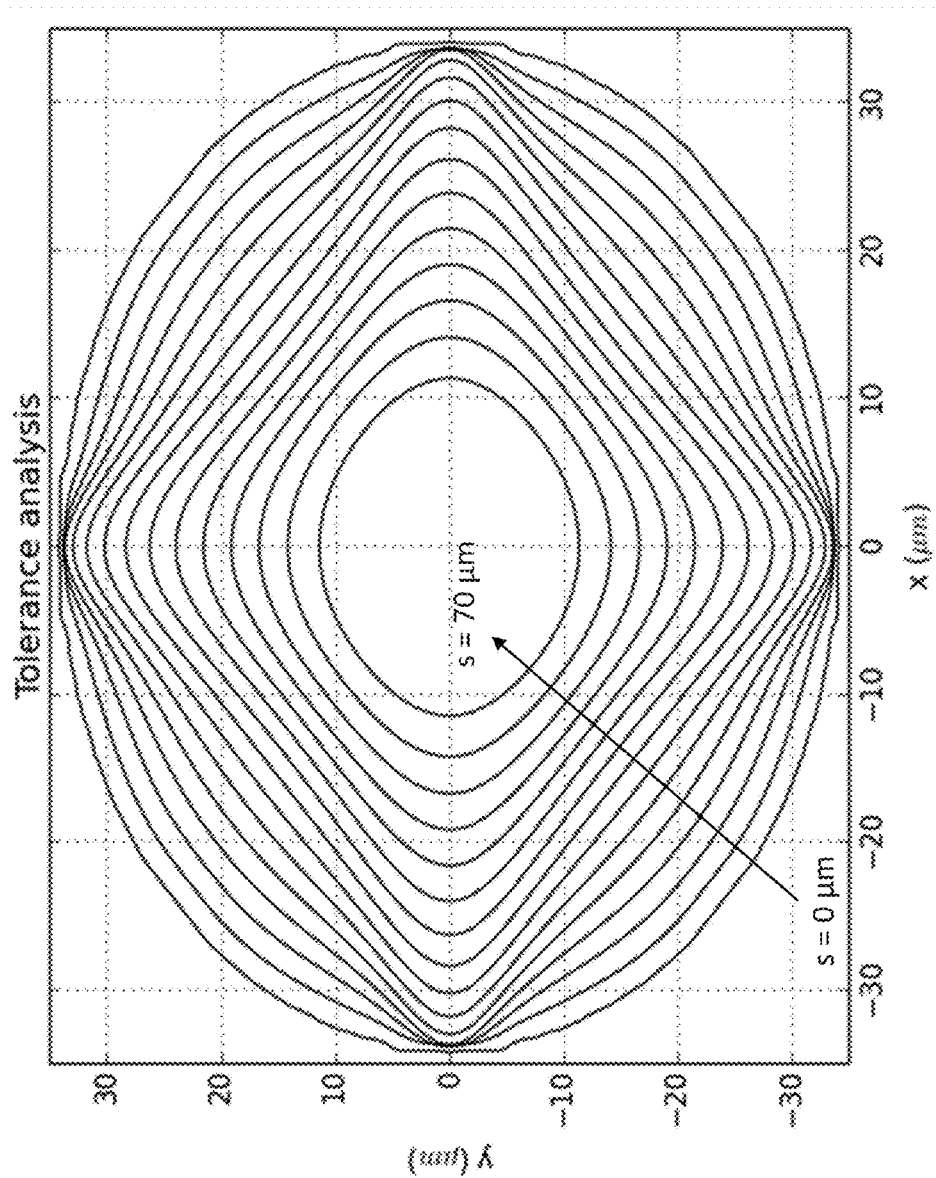
FIG. 18 illustrates simulated spatial tolerances based on separation distance, according to an embodiment.

The permissible tolerances in order to achieve a coupling efficiency greater than 95% (0.22 dB coupling loss) as a function of the distance s (from 0 to 70 µm with 5 step) can be seen in FIG. 18, according to one example. Attending to the spatial tolerance values in the order of several µm, the alignment between the PIC 10 and photodiode array 3 can be passive, i.e., no need of monitoring the photo-current detected by photodiode array 3 during the alignment, even considering a separation distance s=70 µm.

Thermal Management

A custom thermal design is required to dissipate the large heat load generated by PIC 10. Otherwise, the base temperature of PIC 10 will increase and effects such as the stress mediated by the material thermal expansions will result in misalignment between parts. Moreover, thermal effects in silicon such as the two-photon absorption will impact on the optical performance of PIC 10, degrading the final SNR.

Figure 19:
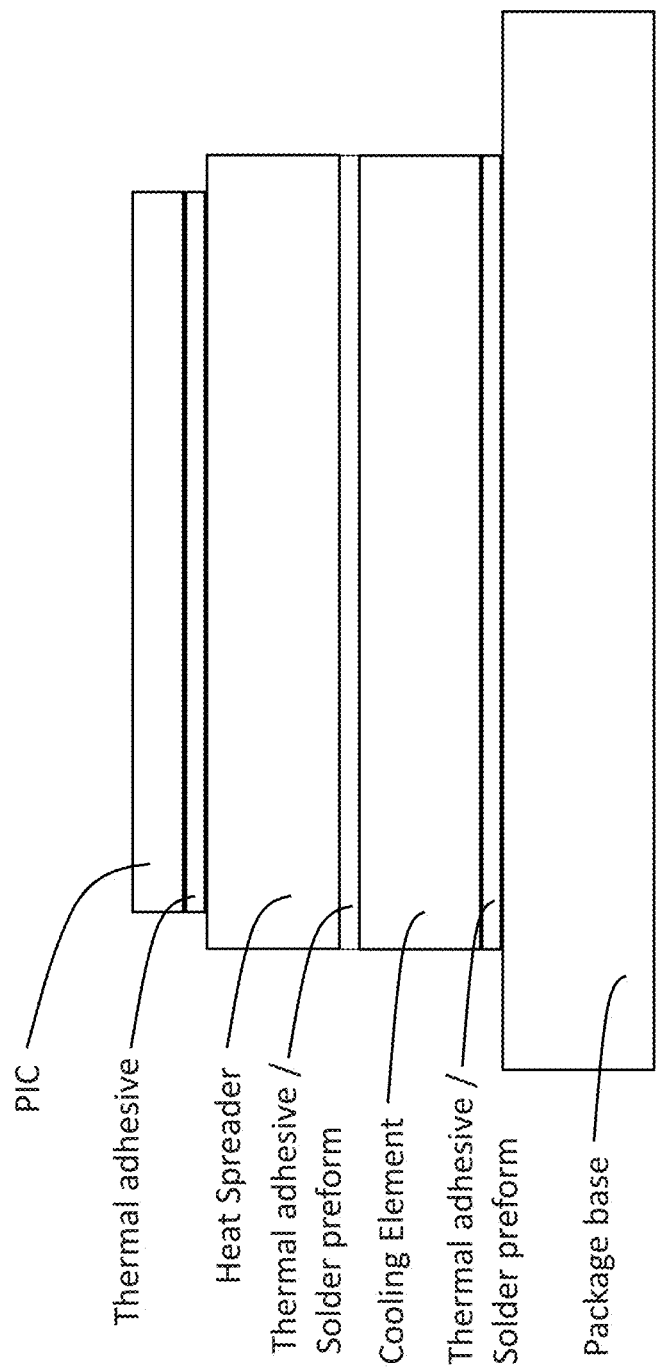
FIG. 19 illustrates a stacked heat sink design, according to an embodiment.

The temperature on the top side of heat spreader 4 should be kept fixed to avoid lack of optical performance depending on the temperature due to undesired misalignments. An example stack of materials considered for the thermal design of a heat sink is shown in FIG. 19. The heat sink includes both heat spreader 4 and cooling element 9, according to an embodiment. The total amount of heat transferred from the heat source through the heat sink should be maximized. The thermal resistances of the PIC 10, heat spreader 4, cooling element 9, and the base of chip package 100 may be fixed by manufacturing materials and thickness. In one example, the PIC has a thickness around 0.67 mm, the heat spreader has a thickness around 1.75 mm, and the cooling element has a thickness around 1.6 mm. The heat load (Q) to be dissipated is about 20 W, according to one example. If the heat sink can manage the dissipation of a temperature gradient (ΔT) with respect to the room temperature, then the total thermal resistance (Rt) must be lower than:

$$R_t\left[\frac{k}{W}\right] < \frac{\Delta T[k]}{Q[W]} \quad (2)$$

Where $R_t$ is the sum of all the thermal resistances corresponding to the stack of materials given in Equation (3):

$$R_t\left[\frac{k}{W}\right] = R_{PIC} + R_{A1} + R_{HS} + R_{A2} + R_{TEC} + R_{A3} + R_{PB} + R_{base} \quad (3)$$

Where $R_{PIC}$, $R_{HS}$, $R_{TEC}$, and $R_{base}$ are thermal resistances of the PIC, heat spreader, cooling element, and chip package base, respectively. Also, $R_{A1}$, $R_{A2}$, and $R_{A3}$ are thermal resistances of the adhesive layers. Thus, the thermal resistance may be defined as:

$$R_t\left[\frac{k}{W}\right] = \frac{t[m]}{A[m^2]\cdot\sigma\left[\frac{W}{m\cdot k}\right]} \quad (4)$$

With t being the thickness, A the cross-sectional area and a the thermal conductivity, respectively. Consequently, the thickness and the material for the parameters $R_{A1}$, $R_{A2}$ and $R_{A3}$ should be properly designed. The bond-line thickness is at the end limited by the planarity of parts positioned up and down and the thermal conductivity and depends on the material. Generally, solder preforms featuring the same thickness than an adhesive result in lower thermal resistances. The main factor limiting the thermal performance of an adhesive is the proportion of voids in a certain volume.

Hermeticity

Moisture penetrating the package results in corrosion and internal condensation (depending on ambient conditions). Generally, the presence of moisture at an interface between dissimilar metals accelerates corrosion. Additionally, epoxy joints being affected as moisture is absorbed translates into potentially weakening the joints; therefore causing performance drops as the epoxy expands. Moisture penetrating the package results in corrosion and internal condensation (depending on ambient conditions). Therefore, an hermetic solution would be highly desired.

Fully hermetic solutions involve very complex part design and assembly steps, driving up the total cost. Consequently, quasi-hermetic approaches are usually assembled in the industry. The larger the degree of hermeticity, the larger the cost will become.

Hermeticity in electro-optical packaging is defined as the leakage rate measured in cm³ per second at a certain atmospheric pressure. A large degree of hermeticity is determined by the package design and manufacturing. As an exemplary case, FIG. 2 shows the hermeticity value reached by the package (<1·10⁻⁸ atm·cm³/s). However, this value will depend on the quality of the lid sealing and the solder performance of the optical window to the package and the metal ferrule of the fiber mount element to the pipe, according to an embodiment. A typical degree of hermeticity used by the laser industry, which involves the packaging of electro-optical components is <1·10⁻⁸ atm·cm³/s.

Delay and Dispersion Balance

Sample and reference arms in an OCT system interferometer must be balanced in terms of accumulated delay and dispersion. As the optical subassembly may be subject to different designs, it may be important to implement an adjustable delay and dispersion compensation system in the reference arm. In this way, the PIC design would be transparent to the scanning unit design.

Figure 20:
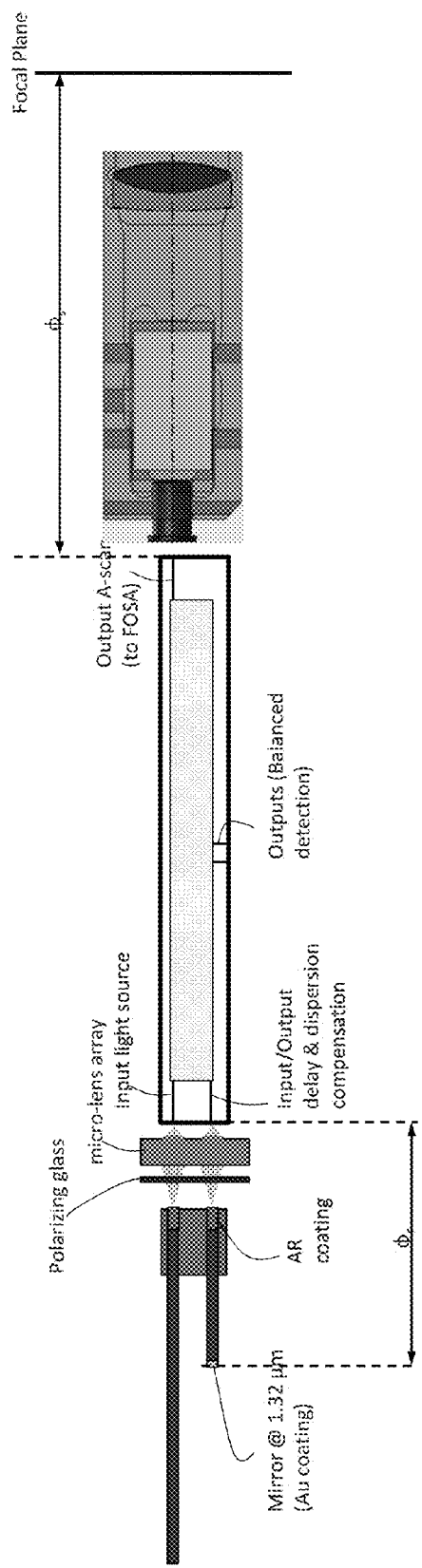
FIG. 20 illustrates balanced sample and reference arms of an interferometer, according to an embodiment.

Both sample and reference arms are balanced on-chip in the particular design of FIG. 1. As a consequence, the effect of the scanning unit 13 is required to be compensated somewhat in the reference arm. For this purpose, an optical fiber with a mirrored end (fiber 15b in FIG. 1) has been implemented in the reference arm as illustrated in FIG. 8. FIG. 20 shows this concept.

The accumulated phase as a function of the wavelength for both the sample and reference arms should be equal, as depicted in Equation (5) below.

$$\Phi_s(\lambda) = \Phi_r(\lambda) \rightarrow \frac{2\pi}{\lambda_0} \sum_{i=1}^{N} n_i(\lambda) \cdot L_i = \frac{2\pi}{\lambda_0} \sum_{j=1}^{M} n_j(\lambda) \cdot L_j \quad (5)$$

Delay imbalance beyond the coherence length along the axial scanning range does not allow for OCT interference generation, and thus, the system becomes generally unusable. Fine adjustment may be performed by means of thermo-optical actuators within the PIC, at the expense of higher power consumption.

On the other hand, the importance of compensating dispersion relies on the loss of OCT axial resolution. Actually, according to Eq. 6, the higher the dispersion imbalance, the wider the full-width-half-maximum (FWHM) of the axial point spread function (PSF) becomes.

$$\sigma_T = [\sigma_C^2 + \{(D_{Si}L_{Si} + Dl_{system})\Delta\lambda c\}^2]^{1/2} \quad (6)$$

where c is the speed of light in vacuum, $\Delta\lambda$ the source bandwidth, $D_{Si}$ the group velocity dispersion (GVD) in silicon, $L_{Si}$ half of the length difference between the arms in silicon, $Dl_{system}$ all the extra dispersive components in the system (dispersion*length) that contribute to the PSF broadening and finally, $\sigma_C$ stands for the coherence length defined by:

$$\sigma_C = \frac{2\ln 2}{\pi} \frac{\lambda_0^2}{\Delta\lambda} \quad (7)$$

Read-Out Output Signals

Very low-amplitude signals are detected at the output of a typical OCT system. If these signals would be directly connected to the package pins, then the signals would be too weak to be useable.

Figure 21:
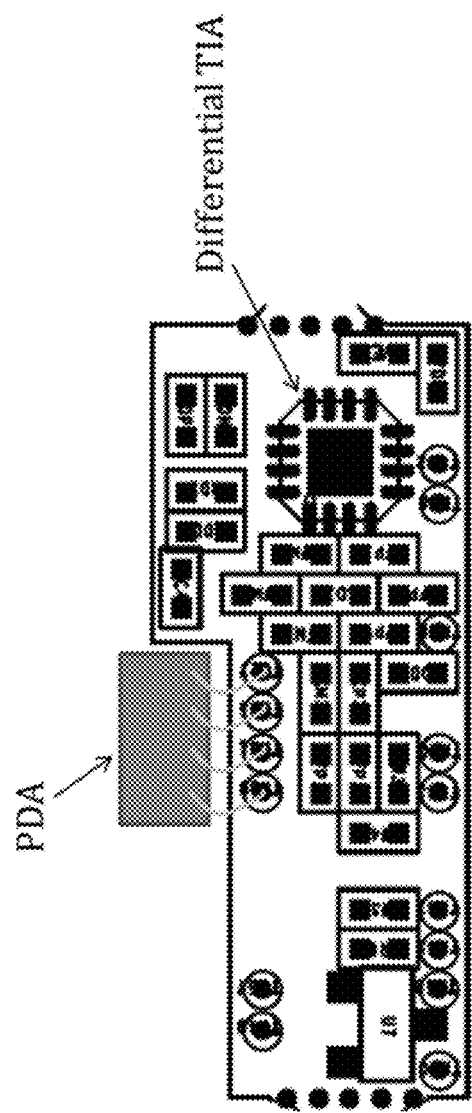
FIG. 21 illustrates an example assembly of a circuit board and photodiode array, according to an embodiment.

According to an embodiment, photodiode array 3 translates light combined from sample and reference paths into electrical interference patters with peak amplitudes in the microamp range and frequencies above Megahertz range. These weak differential signals should be amplified before exiting the package so as to avoid SNR degradation. An impedance adaptation network followed by a differential low-noise Trans Impedance Amplifier (TIA) can raise the weak signals up to the millivolt range (TIA gain above 80K) and also keep the noise floor low which maximizes the SNR. The electronics are included on a circuit board that is glued onto the heat spreader, very close to the photodiode array in order to shorten the length of wires, as illustrated in FIG. 21. The design also includes well adapted monitor outputs for alignment and verification procedures.

Lateral Scanning and Focusing

Figure 22:
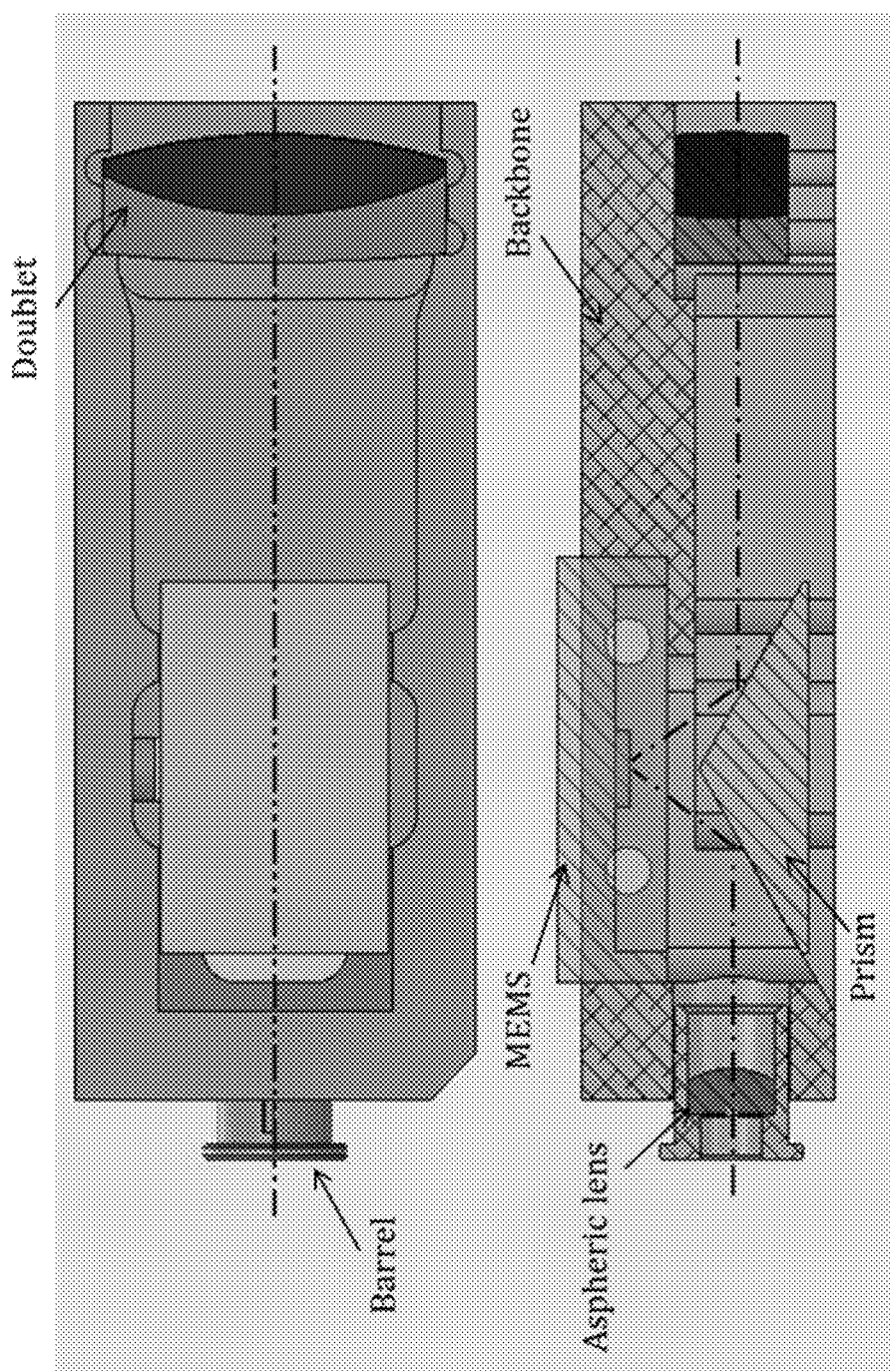
FIG. 22 illustrates an example assembly of a scanning unit, according to an embodiment.

According to an embodiment, the PIC 1 implements depth-scans (A-scan) while the scanning unit 13 implements lateral scanning capability (B-scan). Scanning unit 13 provides a desired scanning range at a designed focal plane outside of the chip package. Moreover, the lateral resolution fulfilling the required depth of field should also be implemented by scanning unit 13. An example assembly of scanning unit 13 is depicted in FIG. 22. The housing is built by two stainless steel pieces, the barrel and the backbone, according to an embodiment. The barrel accounts for the beam collimator which includes an aspherical lens inside. The backbone accounts for the lateral scanner, performed by a 60 degrees angled prism and one magnetic MEMS; and also the focusing optics by means of a doublet element, according to an embodiment. The beam of light that exits from the PIC 10 is collimated at scanning unit 13 with the aspheric lens, and then is sent to the prism that is located below the MEMs mirror. The beam of light is then sent to the focusing doublet lens and finally exits the chip package through optical window 14.

As already mentioned, optical delay and dispersion should be balanced in OCT systems. A fiber with a mirror end is used in reference to compensate delay and dispersion induced by scanning unit 13. However, fiber cut tolerances are about 1 mm which is almost half of the axial scanning range. In order to compensate such tolerance, the barrel of the scanning unit may be extracted/inserted into the backbone and thus, increase or decrease the sample optical path without affecting the scanning range or resolution, according to an embodiment.

An assembly tolerance analysis (from 36-90 degrees of operation temperature) may be performed according to the tolerances provided by the manufacturers of the optical components. The criterion that is set for the tolerance analysis is the RMS spot radius. According to one example, the results indicate that: (1) in order not to exceed the ±1 mm from the nominal focus position, the tolerance on the distance between the source and the asphere is about ±0.02 mm; (2) the tolerance on decentre of the asphere is ±0.05 mm and on the tilt tolerance is ±0.1 degrees; (3) the tolerance on the tilt of the MEMs mirror in the non-scanning direction is ±0.7 degrees. For larger values the beam is being clipped on the doublet; and (4) the tolerance on decentre of the entire backbone with respect to the source on both axes is ±0.05 mm and on the tilts is ±0.5 degrees. Therefore, active alignment between PIC 10 and the scanning unit 13 may be required.

Polarization

Light traveling through the one or more waveguides on the PIC 10 suffers from polarization rotation along both, the sample and reference paths of the interferometer. Even if a linear TE polarization, with high PER (polarization extinction ratio) is launched into the PIC 10, structures like bends or curves will transfer part of the energy into the orthogonal polarization (TM). The birefringence in silicon induces significant delay difference between both polarizations. Such delay difference translates into undesired double OCT images after these polarizations beats in the detector.

Suppressing the undesired polarization prior to detection is one solution to avoid double OCT images. A polarizing element 7 is employed for the orthogonal and undesired polarization suppression, according to an embodiment. On one side, polarizing element 7 assures that only the light aligned along the main polarization axis will enter the PIC 10. This way, high PER is guaranteed and thus, polarization beatings across the PIC 10 are minimized. On the other side, light coupled in/out of the reference fiber (e.g., 15b) is filtered in the same way. Polarization rotation from the reference fiber coupling into the PIC and into the detector is depreciable. Therefore, the reference path provides a linear and clean polarization. Even if the sample path transfers energy into the undesired polarization by rotation, only the desired polarization will be beaten with reference in the photodetector and thus, no double images will be generated.

Wire Bonding

The axial scanning (A-scan) may be carried out by means of thermo-optical effects in silicon, according to an embodiment. High density molybdenum heaters deposited along the waveguides may provide heat transfer to perform the full axial scan. Au/Al contact pads may be used to connect these heaters to the package pins.

Figure 23:
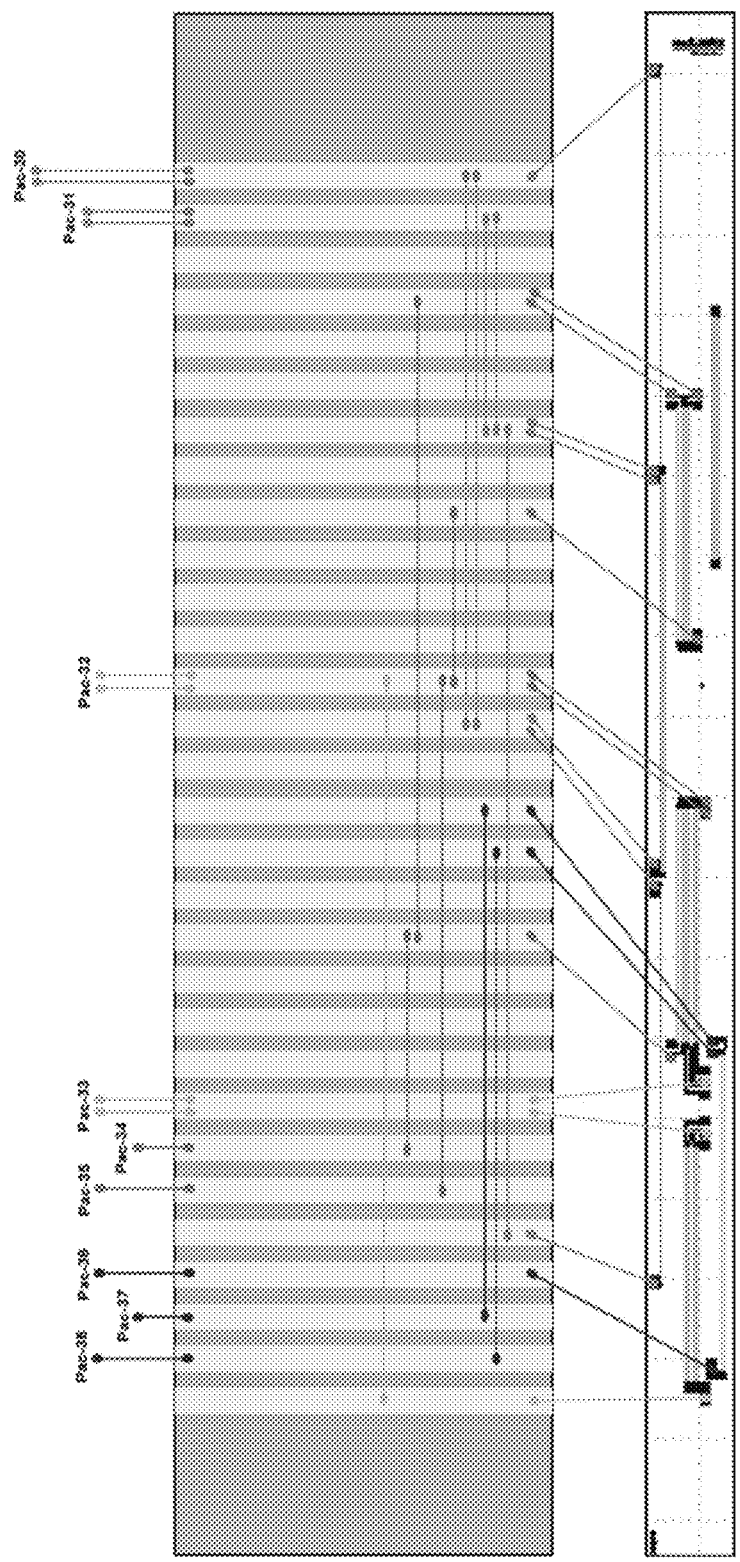
FIG. 23 illustrates an example wire bonding scheme.

The large number of contact pads, among others, complicates the wire-bonding process directly from the PIC 10 to the pins of the chip package. One solution aims at using interposer 11 as illustrated in FIG. 23. Such an element provides a connection map between the PIC 10 and package pins. It can combine and, therefore, simplify wire connections coming from various elements used in particular structures. Interposer 11 decreases the wires length and also, facilitates the use of multiple wires so as to reduce the current density.

Chip Package Assembly

The various components within chip package 100 are assembled and aligned to maximize the use of space within housing 1 and to maximize coupling efficiency of a beam of light passing between the various optical components, according to an embodiment. PIC 10 may first be bonded to heat spreader 4, which acts as an upper layer of a heat sink. The heat sink may also include a cooling element bonded to the interior of housing 1. Solder may be used for attaching the heat sink to the housing interior of chip package 100.

Photodiode array 3 should be aligned with an optical output from PIC 10 and placed into the chip package, according to an embodiment. Careful alignment of photodiode array 3 may be carried out using a process depicted generally in FIGS. 24-28, according to an embodiment.

Figure 24:
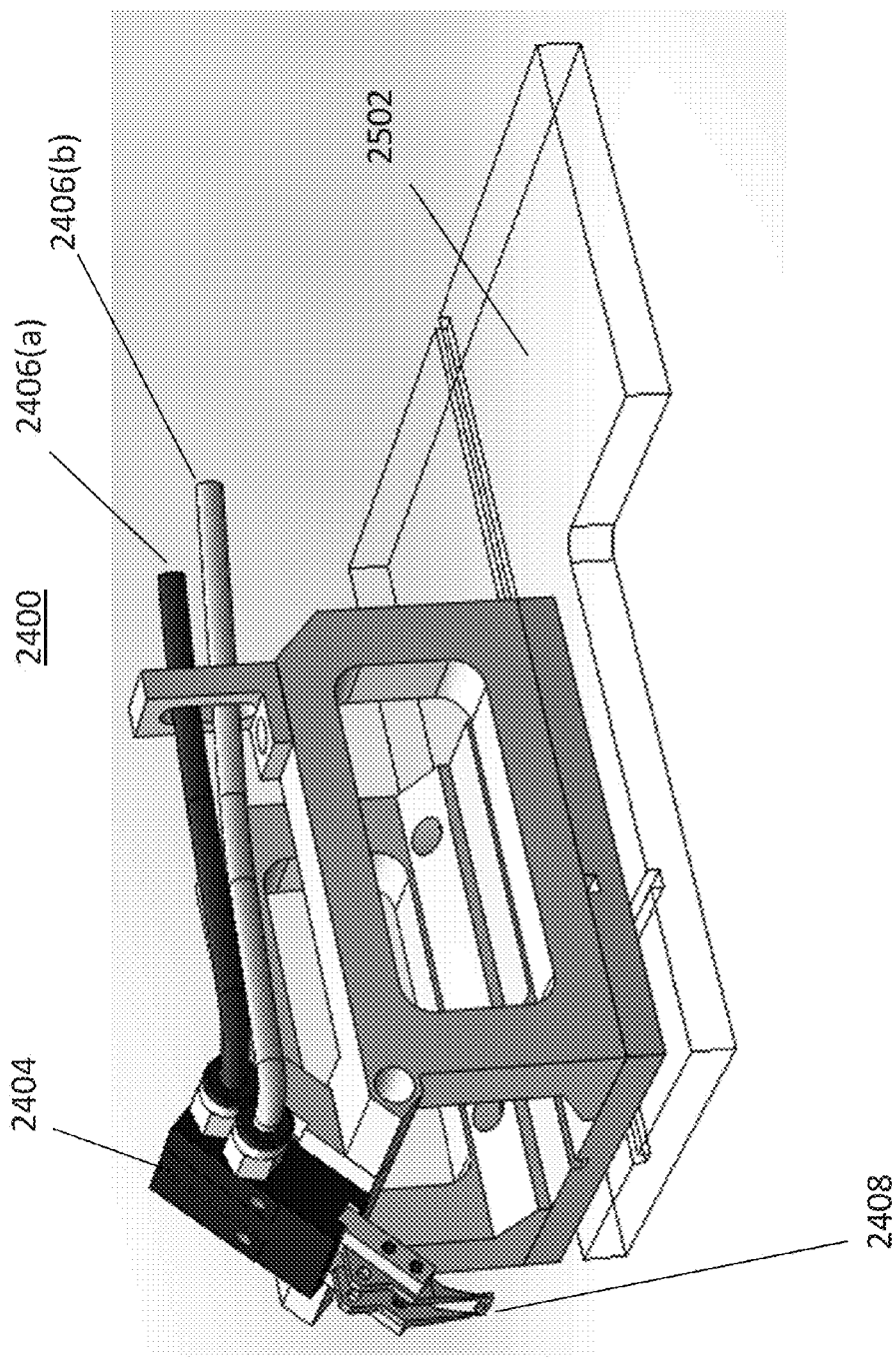
FIG. 24 illustrates an example assembly for placing an element within a package.
Figure 25:
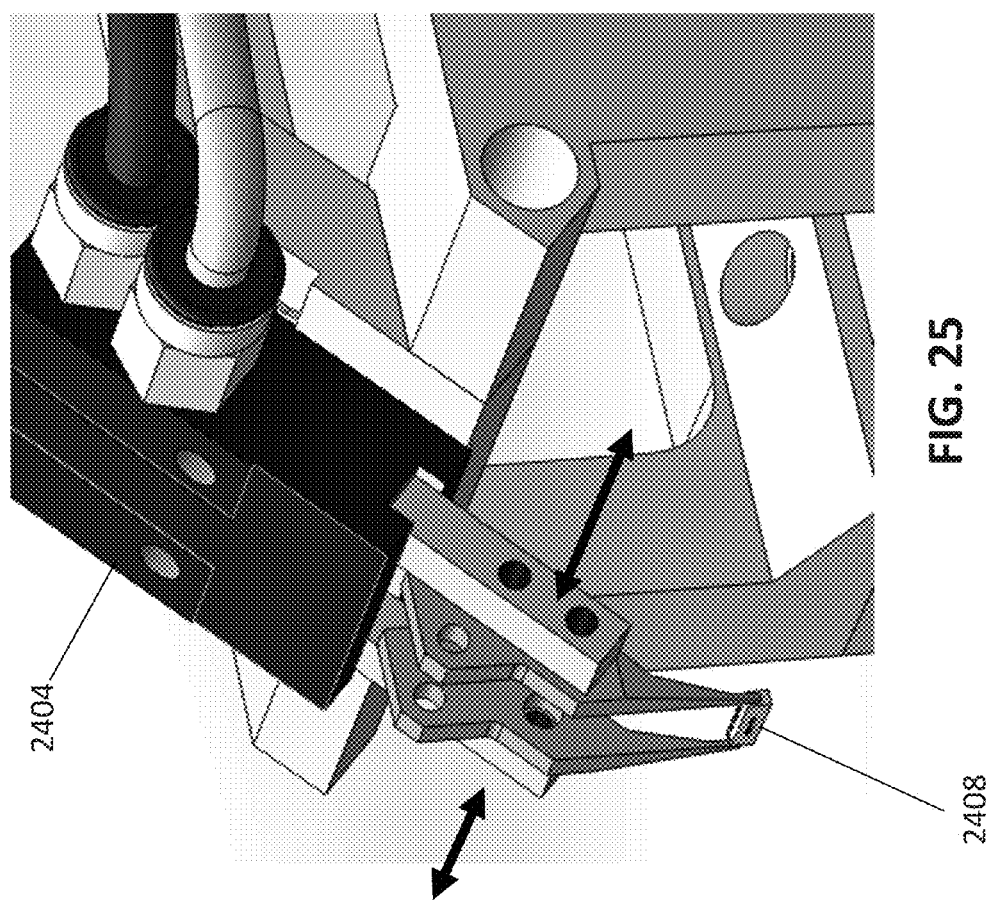
FIG. 25 illustrates another view of the example assembly for placing an element within a package.

FIG. 24 illustrates an alignment tool 2400 that includes a 6-axis platform 2402, a gripper body 2404, and pneumatic lines 2406a and 2406b used to open and close the jaws of gripper body 2404. Gripper body 2404 is designed to hold a specific part 2408 to be aligned. In this case, part 2408 is the photodiode array 3 as shown more clearly in the close up view of gripper body 2404 illustrated in FIG. 25. FIG. 25 also shows with the double-ended arrows the movement of the pincers that hold and release part 2408.

Figure 26:
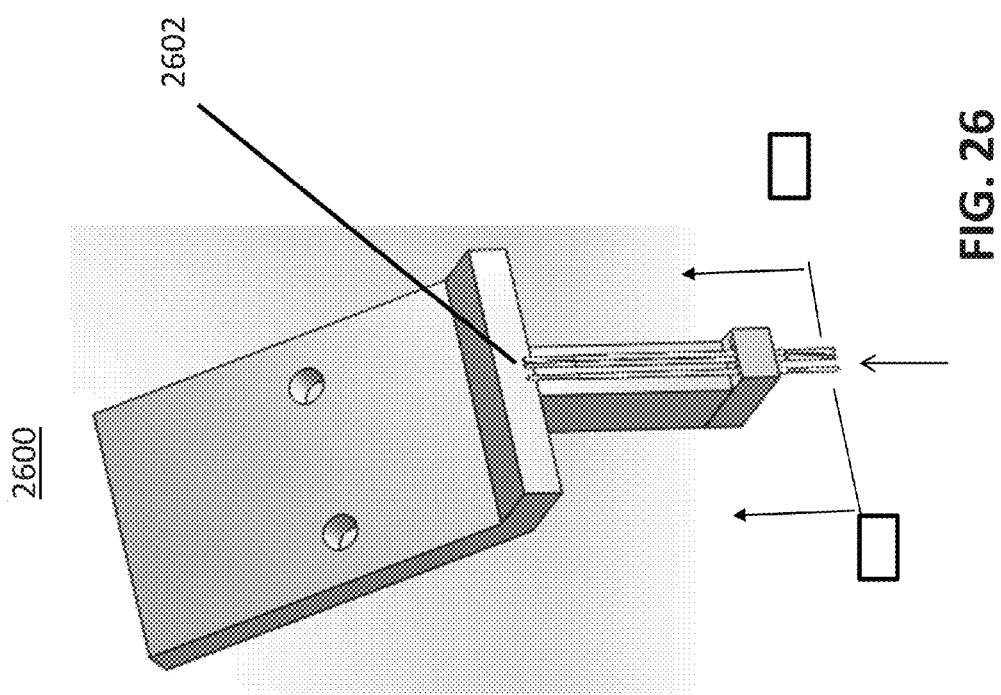
FIG. 26 illustrates a mounting bracket, according to an embodiment.

FIG. 26 illustrates a clamp structure 2600 that includes a set of pogo-style pins 2602. The bottom part of pins 2602 make contact with part 2408 while the top part of pins 2602 can attach to electrical flying leads to be connected to external testing equipment, according to an embodiment. Pins 2602 may have a pitch around 0.5 mm.

Figure 27:
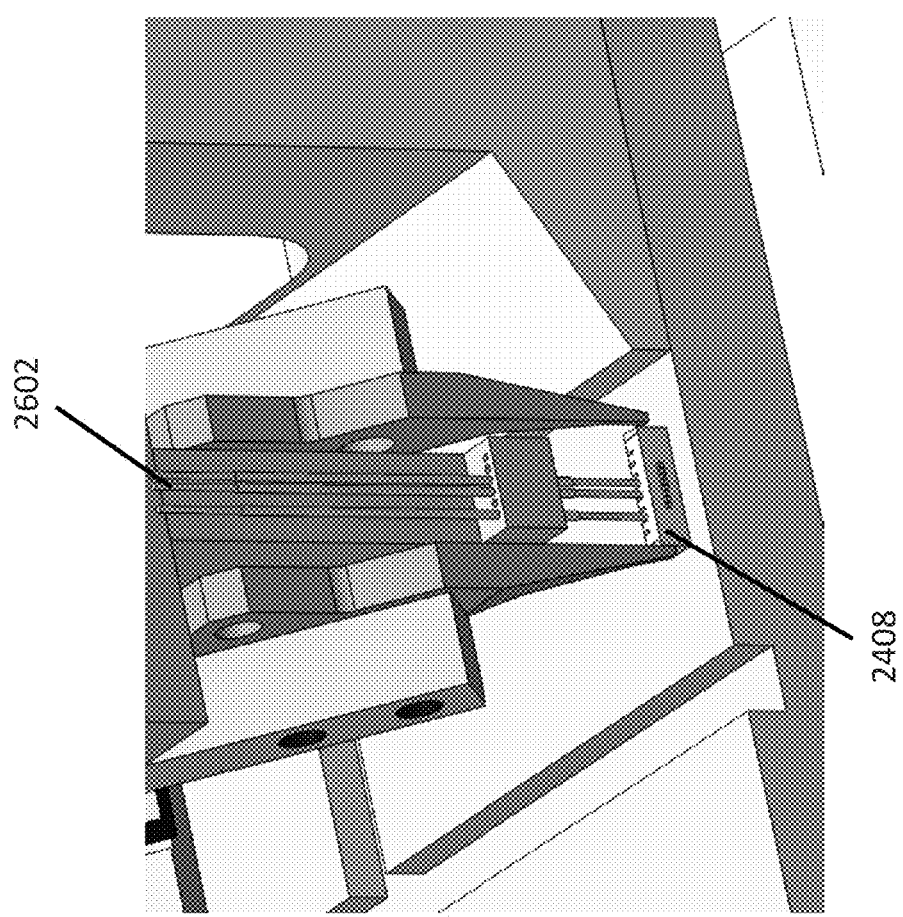
FIG. 27 illustrates the mounting bracket with the example assembly for placing an element within a package, according to an embodiment.
Figure 28:
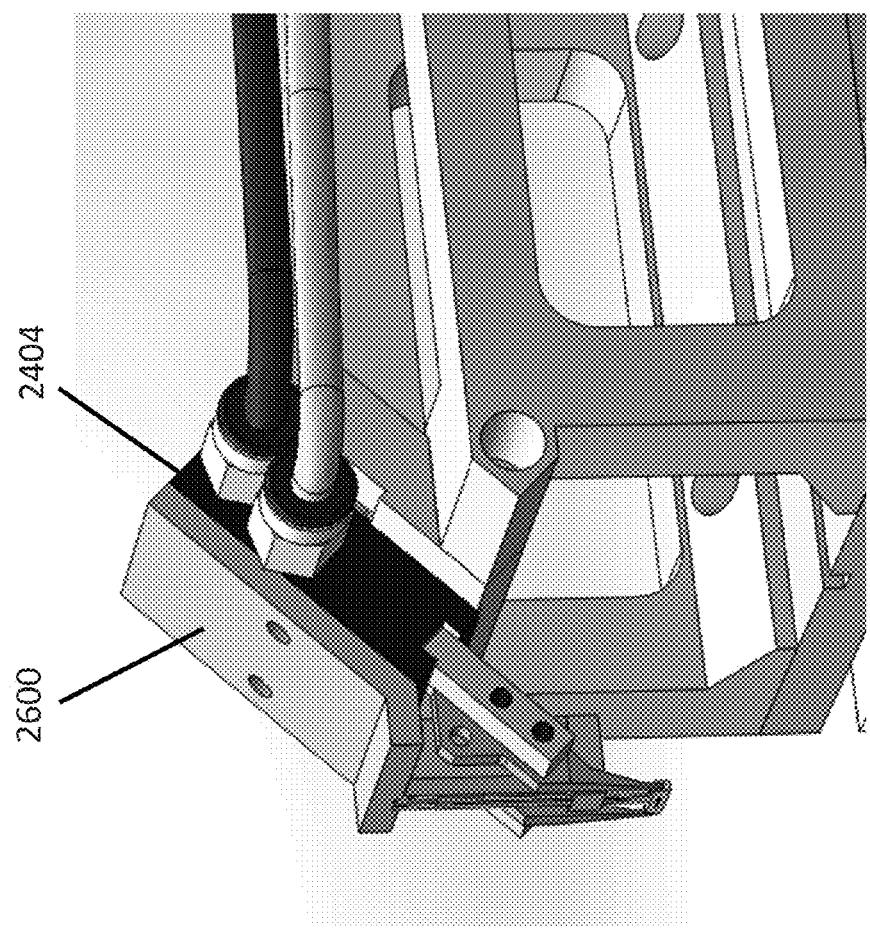
FIG. 28 illustrates another view of the mounting bracket with the example assembly for placing an element within a package, according to an embodiment.

FIG. 27 illustrates the connection made between pins 2602 and part 2408. In this example, part 2408 is a photodiode array to be placed within chip package 100. FIG. 28 displays another view where clamp structure 2600 is seen resting over gripper body 2404.

Once the photodiode array has been carefully aligned and placed within chip package 100, lens array 8 is aligned to PIC 10 as well, and placed within chip package 100. In order to facilitate the handling of lens array 8, lens array 8 may first be attached to a post, according to an embodiment. The post is then mechanically manipulated to align the lens array with the waveguides on PIC 10.

Figure 29:
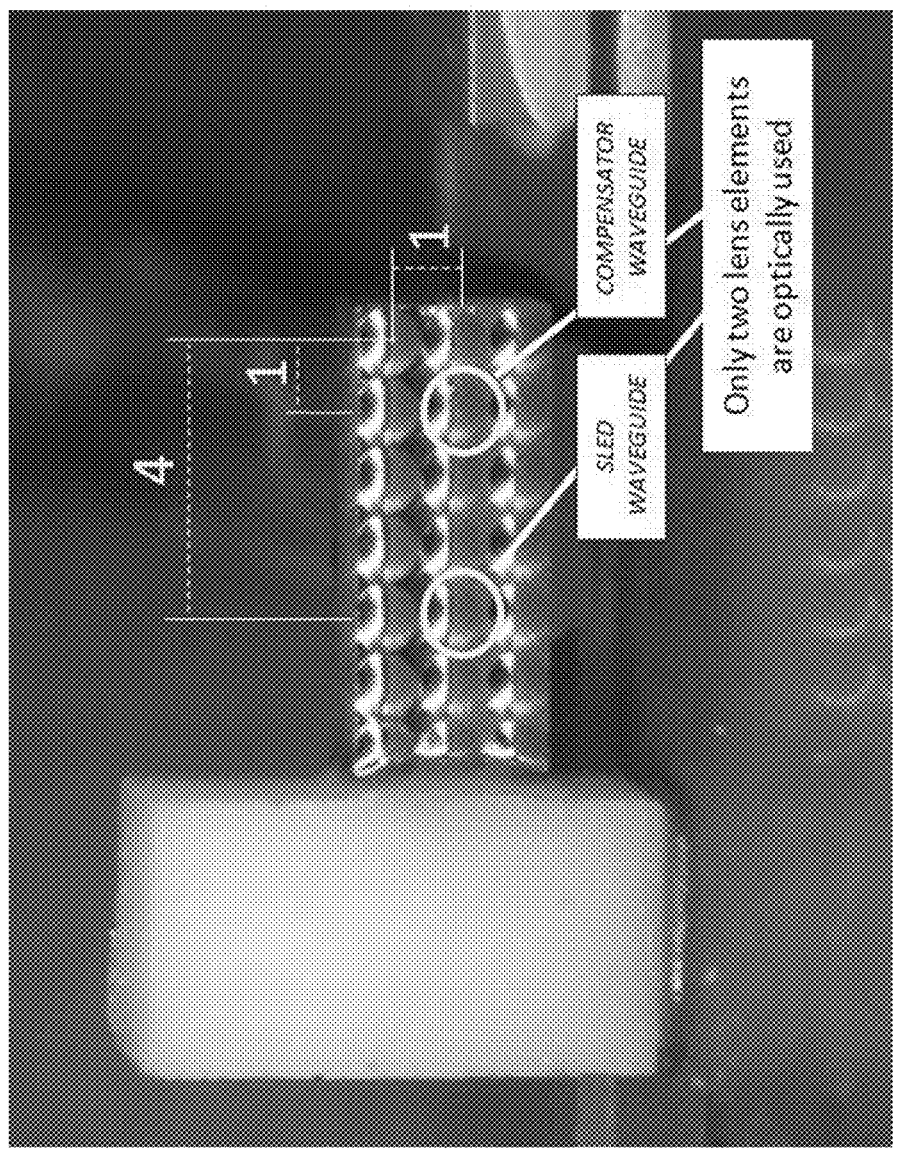
FIGS. 29-31 illustrate various stages of assembling and aligning a lens array, according to an embodiment.
Figure 30:
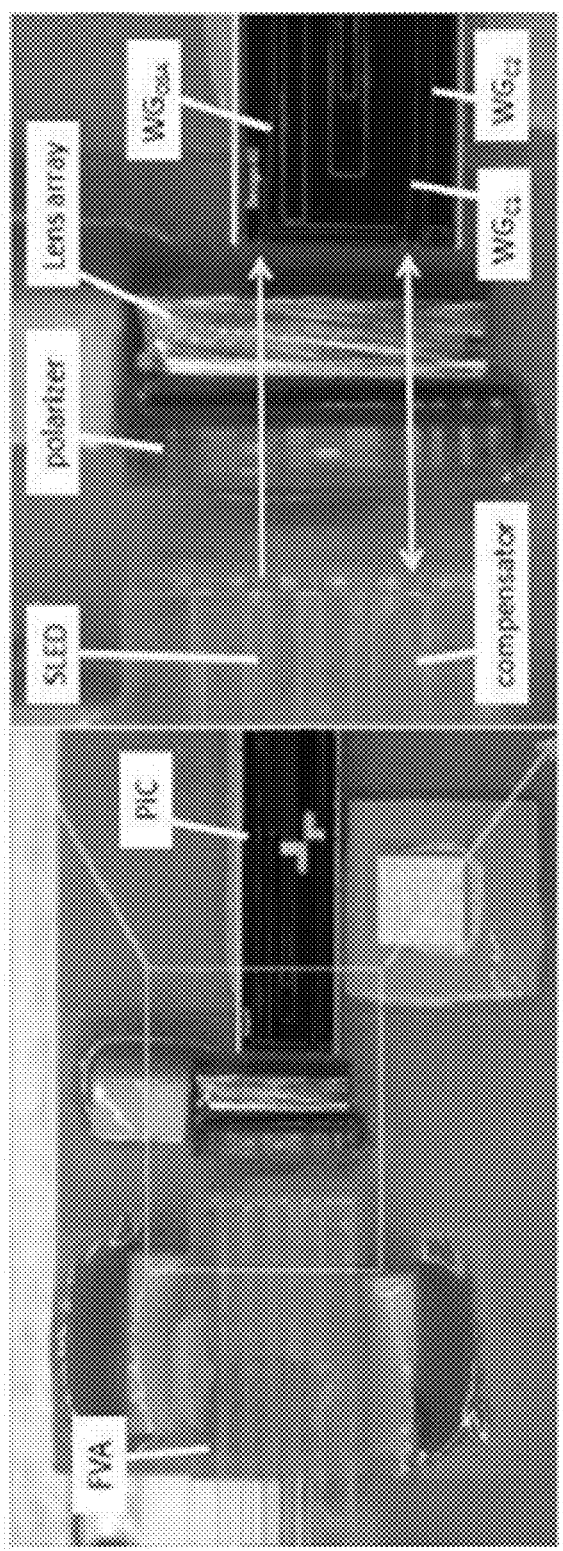
Figure 31:
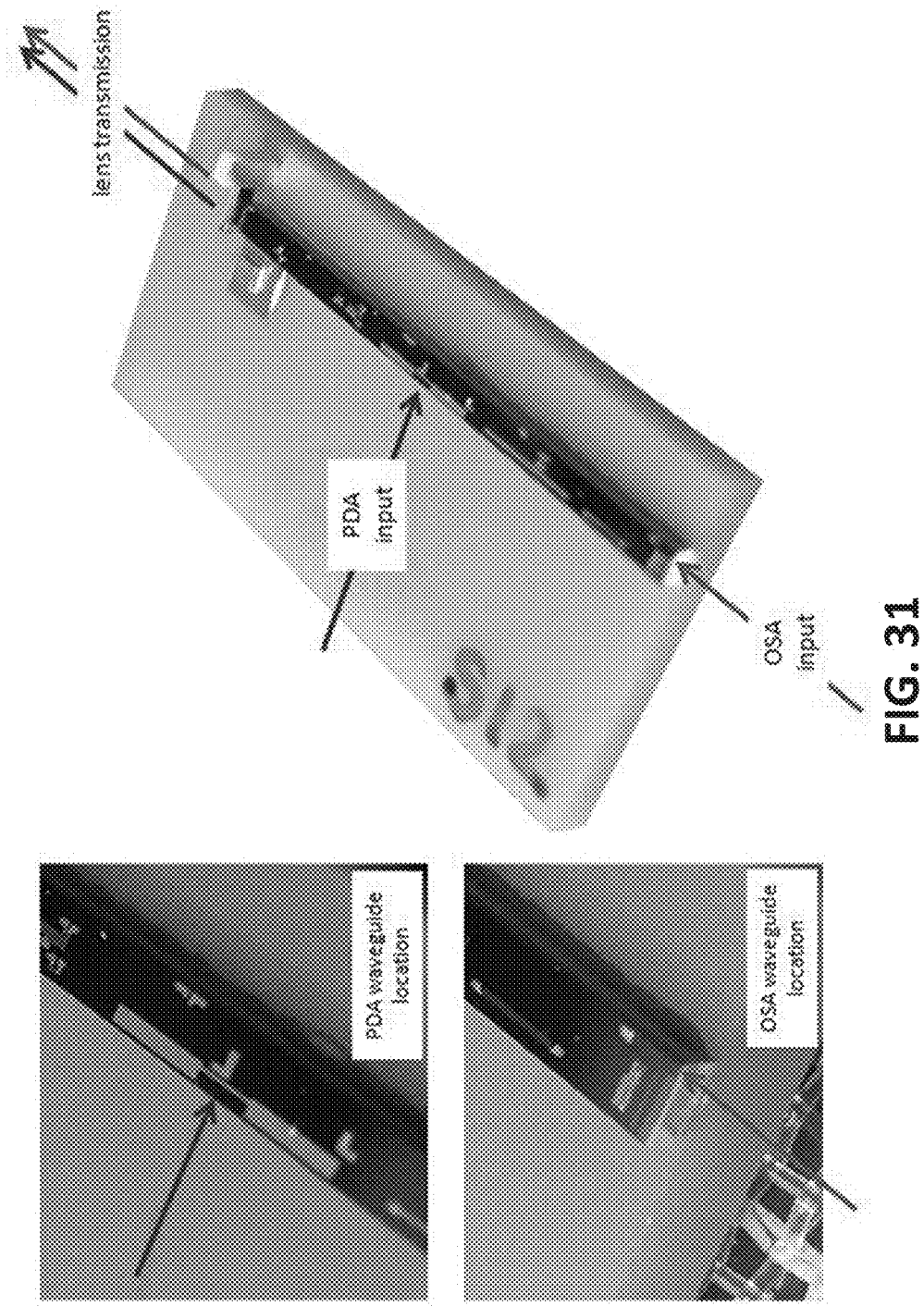

The alignment procedure of lens array 8 does not involve active coupling to optical fibers which would be extremely complex. Instead an optical beam profiler is used to launch optical power into the PIC in the reverse direction compared to how light is guided in the fully completed module, according to an embodiment. In this way, optical power is made to emit from the PIC inputs, which then transmits through the lens array in the reverse direction during active alignment. The optical power that is transmitted from the lens array is detected on a distant beam profiler. This set up is illustrated in FIGS. 29 and 30, with the lens elements actually be used in the alignment circled in FIG. 29. Furthermore, FIG. 31 shows this reverse optical routing concept through the PIC. The shape of the beam footprints that are incident on the profiler can be used to infer collimation and off-axis misalignments. This information allows lens array 8 to be optimally aligned, followed with adhesive attach to the heat sink.

Figure 32:
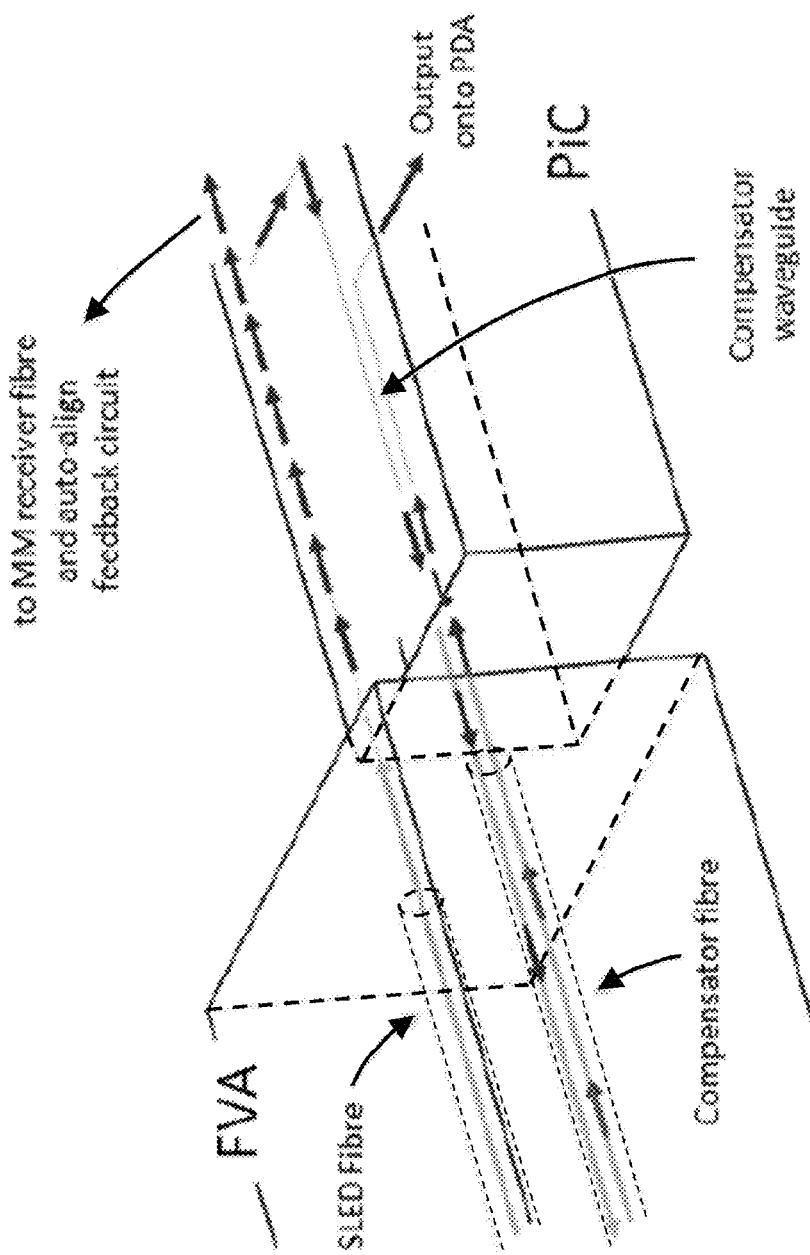
FIGS. 32 and 33 illustrate the alignment of a fiber mount to waveguide of a photoninc integrated circuit, according to an embodiment.

Next, the fiber mount 6 may be aligned and attached, such that optical fibers mounted in the fiber mount are aligned to the lens array 8. The placement of fiber mount 6 may be important for the overall operation since it aligns the optical fibers (15a and 15b) to the waveguides on PIC 10. FIG. 32 illustrates the positions and optical routing corresponding to a well aligned optical assembly of a fiber mount ('FVA' in the figure) to a PIC. Initially, the FVA source fibre ('SLED' in the figure) is aligned to the PIC Compensator waveguide. A photocurrent signal may be used to determine when the FVA is optimally aligned. Next, the FVA is manually translated horizontally that the source fibre is aligned approximately with a different PIC waveguide.

Figure 33:
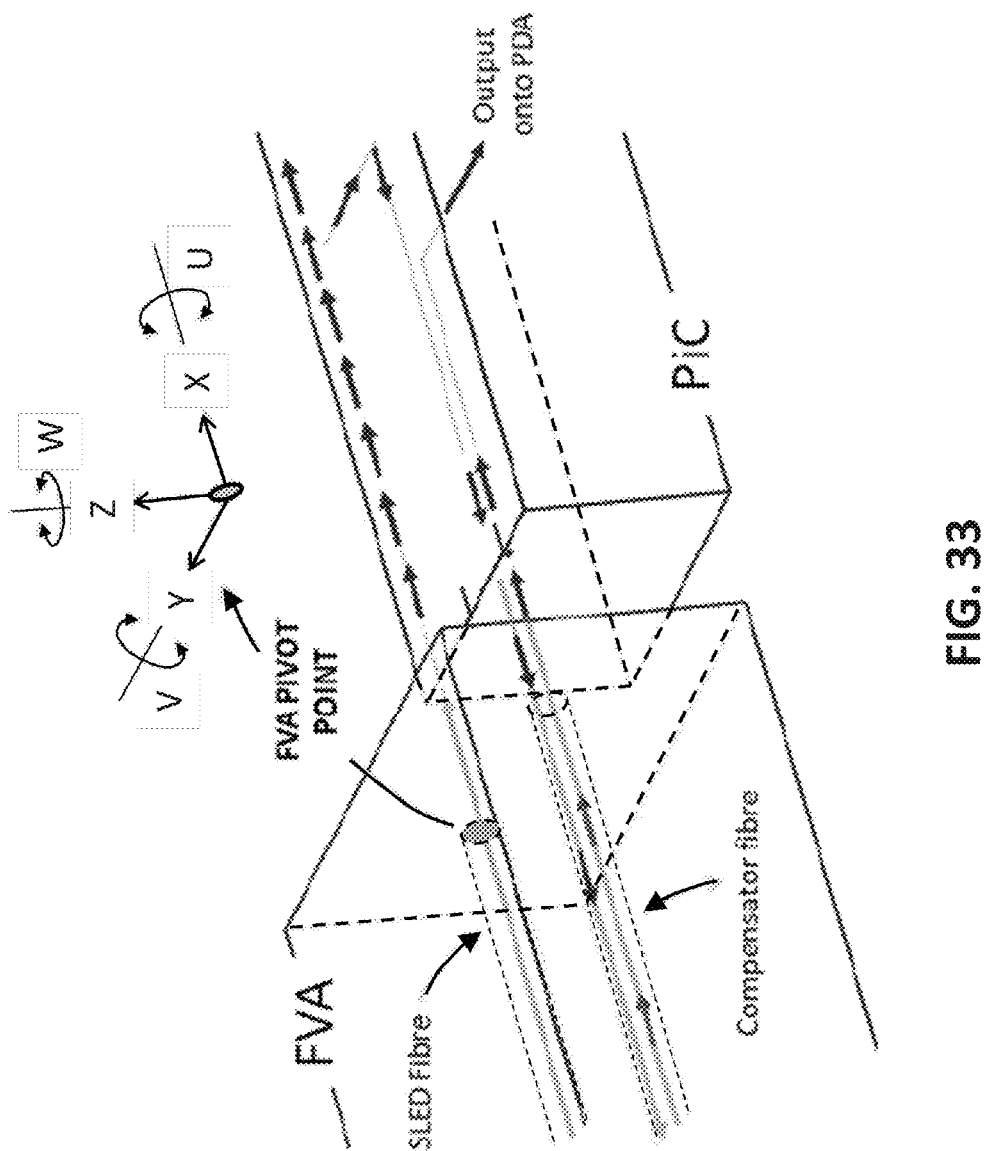

A lens assembly may then be used and, by manipulating the position of the lens relative to the PIC output, a pseudo-collimated beam can be generated. By translating the lens position left/right in the package, the beam can be made to steer approximately along the axis of the package and emerge centrally from the package window aperture. A multimode fibre assembly is placed in line with this beam, outside the package, in order to collect some of this light. In this way, optimal rotation angles can be found as illustrated schematically in FIG. 33.

Afterwards, scanning unit 13 may be aligned and attached using a similar alignment arrangement as depicted in FIGS. 24-28. The alignment between scanning unit 13, PIC 10, photodiode array 3, and optical fibers 15a and 15b is performed so as to maximize a coupling efficiency of a beam of light traveling between each of the components, according to an embodiment.

Wire bonding may be performed to attach the various electrical leads to pins of the chip package. Finally, any seams around the outside of chip package 100 may be sealed to improve hermeticity.

Figure 34:
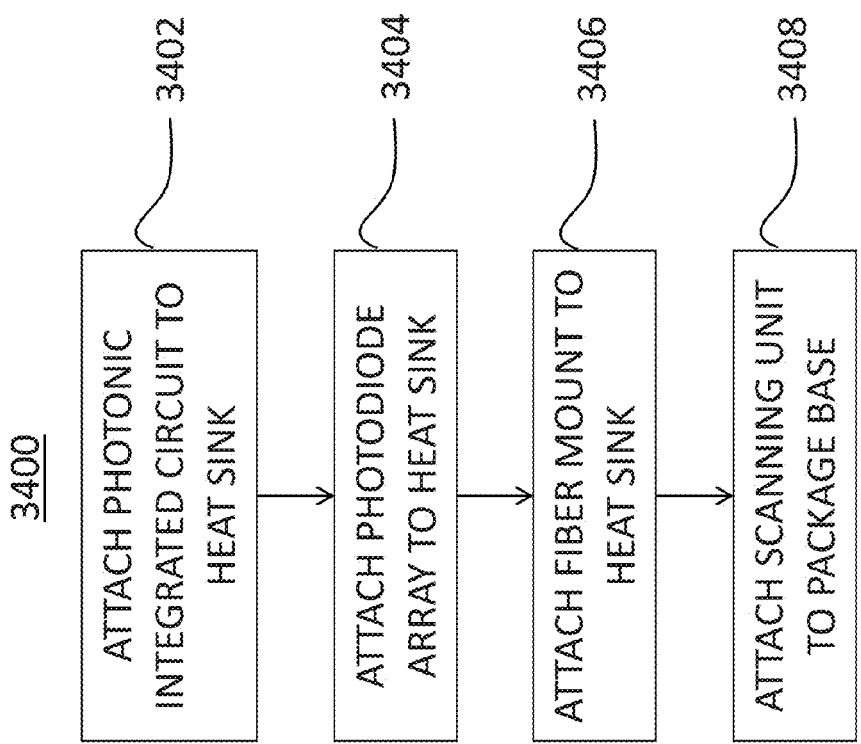
FIG. 34 illustrates a method, according to an embodiment.

FIG. 34 illustrates an example assembly method 3400 for placing various components within a chip package, according to an embodiment.

Method 3400 begins at block 3402 where a photonic integrated circuit (PIC) is attached to a heat sink. The PIC may be attached to a heat spreader layer of the heat sink. The heat sink may already be attached to a base of the chip package. Typically, one side of the PIC includes an active layer including waveguides and opto-electrical components while the opposite side is bonded to the heat sink.

At block 3404, a photodiode array is also attached to the heat sink, according to an embodiment. The photodiode array may be attached to the heat spreader layer of the heat sink. The photodiode array may collectively be called a photodetector. Many types of photodetectors may be used including CMOS based, CCD, reverse-biased LEDs, etc.

At block 3406, a fiber mount is attached to the heat sink, according to an embodiment. The fiber mount may be attached to the heat spreader layer of the heat sink. The fiber mount is attached such that optical fibers are aligned to waveguide inputs on the PIC. A lens array and polarizing element may also be used between the fiber mount and PIC. The lens array should also be aligned between the fiber mount and PIC waveguide to ensure that light is focused correctly onto the waveguide facet on the PIC.

At block 3408, a scanning unit is attached to the package base, according to an embodiment. Each of the PIC, photodiode array, scanning unit, and fiber mount are aligned within the package such that light may be coupled between the elements, and more specifically, so that the coupling efficiency is maximized as light passes between the elements, according to an embodiment.

CLOSING REMARKS

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A chip package comprising:
   a first housing;
   one or more electrical connections coupled to an exterior of the first housing;
   a heat sink coupled to an interior surface of the first housing;
   a photonic integrated circuit coupled to the heat sink and having at least one waveguide configured to guide a beam of light; and
   a scanning unit having a second housing that comprises at least one lens and at least one movable element, the second housing being coupled to the interior surface of the first housing, wherein the scanning unit is configured to laterally scan the beam of light across a focal plane outside of the first housing, and wherein the second housing of the scanning unit is aligned with, and is separate from, the photonic integrated circuit within the first housing such that the beam of light is coupled between the photonic integrated circuit and the scanning unit.

2. The chip package of claim 1, further comprising a fiber mount element configured to hold an optical fiber and align a facet of the optical fiber to the at least one waveguide.

3. The chip package of claim 2, wherein the optical fiber is threaded through a ferrule that extends through one wall of the first housing, and wherein a second facet of the optical fiber is coupled to an optical source.

4. The chip package of claim 3, further comprising one or more additional optical elements disposed within the first housing and between the facet of the optical fiber and the at least one waveguide.

5. The chip package of claim 4, further comprising a polarizing element disposed within the first housing and between the facet of the optical fiber and the one or more additional optical elements.

6. The chip package of claim 4, wherein the one or more additional optical elements include a micro-lens array.

7. The chip package of claim 1, wherein the photonic integrated circuit comprises an interferometer configured to control an A-scan of an optical coherence tomography (OCT) imaging technique.

8. The chip package of claim 7, further comprising a detector configured to receive an optical interference signal from the interferometer.

9. The chip package of claim 7, wherein the scanning unit is configured to control a B-scan of the OCT imaging technique.

10. The chip package of claim 8, wherein the scanning unit is further configured to adjust a resolution of the beam of radiation as the beam of radiation is laterally scanned.

11. The chip package of claim 1, further comprising an optical window in one wall of the first housing, the optical window comprising a material substantially transparent to infrared wavelengths, wherein the scanning unit is aligned such that the beam of light is transmitted from the scanning unit through the optical window.

12. The chip package of claim 1, wherein the scanning unit is configured to provide a scanning range of about 12 mm.

13. The chip package of claim 1, wherein the first housing is hermetically sealed.

14. The chip package of claim 1, further comprising a thermo-electric cooling device disposed within the first housing.

15. The chip package of claim 1, wherein the at least one waveguide is configured to include substantially rounded optical modes having substantially the same numerical aperture for both an x-axis perpendicular to a direction of light propagation, and a y-axis perpendicular to the direction of light propagation.

16. The chip package of claim 1, wherein the heat sink comprises a multilayer structure coupled to an underside of the photonic integrated circuit.

17. The chip package of claim 1, wherein the at least one movable element comprises a mirror actuated by a micro-electromechanical element.

18. The chip package of claim 1, wherein the beam of light is coupled from an output of the photonic integrated circuit to an optical fiber, and wherein the optical fiber terminates with a mirror coating.

19. A method, comprising:
   attaching a heat sink to one side of a photonic integrated circuit, and attaching an opposite side of the heat sink to a base of a package;
   attaching a photo detector to the heat sink;
   attaching a fiber mount to the heat sink;
   attaching a housing of a scanning unit to the base of the package, wherein the housing includes one or more optical elements, and wherein the attaching of the scanning unit, the attaching of the fiber mount, and the attaching of the photo detector align the photonic integrated circuit, photo detector, fiber mount, and scanning unit so as to maximize a coupling efficiency of a beam of light traveling between the photonic integrated circuit, photo detector, fiber mount and scanning unit.

20. The chip package of claim 16, wherein the multilayer structure comprises a heat spreader and a cooling element.

21. The chip package of claim 1, wherein the at least one lens comprises an aspheric lens.

22. The chip package of claim 1, wherein the at least one lens comprises a doublet lens.

23. The chip package of claim 1, wherein the at least one lens and at least one movable element comprises:
- an aspheric lens configured to receive the beam of light from the photonic integrated circuit;
- a movable mirror; and
- a doublet lens configured to focus the beam of light at the focal plane outside of the first housing.

* * * * *